(12) United States Patent
Khodadoust

(10) Patent No.: US 6,204,013 B1
(45) Date of Patent: Mar. 20, 2001

(54) MSP-5 NUCLEIC ACID MOLECULES AND USES THEREFOR

(75) Inventor: Mehran M. Khodadoust, Brookline, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/163,285

(22) Filed: Sep. 29, 1998

Related U.S. Application Data

(60) Provisional application No. 60/090,398, filed on Jun. 23, 1998.

(51) Int. Cl.[7] ............ C07K 14/705; C07K 16/28; C07K 14/47; C12N 1/21; C12N 5/10

(52) U.S. Cl. ............ 435/69.1; 435/69.1; 435/252.3; 435/320.1; 435/325; 530/324; 530/350; 530/330; 530/329; 530/326; 536/23.1; 536/23.5; 536/22.1

(58) Field of Search .................. 435/69.1, 6, 69.7, 435/69.8, 91.4, 252.3, 320.1, 283.1, 285.1, 287.2; 536/23.1, 23.4, 23.5, 24.1, 24.31

(56) References Cited

FOREIGN PATENT DOCUMENTS

| 0845269 A2 | 6/1998 | (EP). |
| WO 99/31131 | 6/1999 | (WO). |

OTHER PUBLICATIONS

Shekhar, Y. C. et al., "Effects of prolonged infusion of human alpha calcitonin gene–related peptide on hemodynamics, renal blood flow and hormone levels in congestive heart failure," American Journal of Cardiology, vol. 67, No. 8, pp. 732–736 (1991).

Thomas, P. B. et al., "Exogenous effects and endogenous production of endothelin in cardiac myocites: potential significance in heart failure," American Journal of Physiology, vol. 271, No. 6/2, pp. H2629–2637 (1996).
Maniatis et al. (1982) Molecular Cloning A Laboratory Manual, Cold Spring Harbor Laboratory. p. 431, 1982.*
Database GenBank on STN, Accession No. W72843, Hillier et al., Oct. 16, 1996.*
Database GenBank on STN, Accession No. AA077497, Touchman et al., Oct. 8, 1996.*
GenBank™ Accession No. AA077497 for Chromosome 7 Fetal Brain cDNA Library *Homo Sapiens* cDNA Clone 7B18G12 (1996).
GenBank™ Accession No. AA296889 for Cerebellum II *Homo Sapiens* cDNA (1997).
GenBank™ Accession No. AA077528 for Chromosome 7 Fetal Brain cDNA Library *Homo Sapiens* cDNA clone 7B44H09 (1996).
GenBank™ Accession No. AA077040 for Chromosome 7 Fetal Brain cDNA Library *Homo Sapiens* cDNA clone 7B07A02 (1996).
GenBank™ Accession No. AA076945 for Chromosome 7 Fetal Brain cDNA Library *Homo Sapiens* cDNA clone 7B05D08 (1996).

(List continued on next page.)

*Primary Examiner*—Christopher S. F. Low
*Assistant Examiner*—Patricia Robinson
(74) *Attorney, Agent, or Firm*—Lahive & Cockfield, LLP; Amy E. Mandragouras, Esq.

(57) ABSTRACT

The invention provides isolated nucleic acid molecules, designated MSP-5 nucleic acid molecules, which encode novel myocardium secreted proteins. The invention also provides antisense nucleic acid molecules, recombinant expression vectors containing MSP-5 nucleic acid molecules, host cells into which the expression vectors have been introduced, and methods for producing MSP-5 polypeptides.

92 Claims, 1 Drawing Sheet

OTHER PUBLICATIONS

GenBank™ Accession No. AA803898 for GM *Drosophila Melanogaster* ovary pOT2 *Drosophila Melanogaster* cDNA Clone GM14561 (1998).
GenBank™ Accession No. AA296961 for Adrenal Gland Tumor *Homo Sapiens* cDNA (1997).
GenBank™ Accession No. AA261570 forSoares Mouse NML *Mus Muscleus* cDNA Clone Image:750576 (1997).
GenBank™ Accession No. AA803448 for GM *Drosophila Melanogaster* ovary pOT2 *Drosophila Melanogaster* cDNA Clone GM13203 (1998).
GenBank™ Accession No. W52850 for Pancreatic Islet *Homo Sapiens* cDNA Clone Image:338679 (1996).
GenBank™ Accession No. W72843 for *Homo Sapiens* cDNA Clone Image 345098 (1996).
GenBank™ Accession No. AA772868 for *Homo Sapiens* cDNA Clone Image:852285 (1998).
GenBank™ Accession No. AA332556 for Embryo, 8 Week I *Homo Sapiens* cDNA (1997).
GenBank™ Accession No. AA056018 for *Homo Sapiens* cDNA Clone Image:377689 (1996).
GenBank™ Accession No. AA661635 for *Homo Sapiens* cDNA Clone Image:1219066 (1997).
GenBank™ Accession No. AA469801 for *Mus Musculus* cDNA Clone Image:849186 (1997).
GenBank™ Accession No. AA630878 for *Homo Sapiens* cDNA Clone Image:1202674 (1997).
GenBank™ Accession No. AA457490 for *Homo Sapiens* cDNA Clone Image:838296 (1997).
GenBank™ Accession No. AA931966 for *Homo Sapiens* cDNA Clone Image:1554388 (1998).
GenBank™ Accession No. W67545 for *Homo Sapiens* cDNA Clone Image:343180 (1996).
GenBank™ Accession No. W67527 for *Homo Sapiens* cDNA Clone Image:343180 (1996).
GenBank™ Accession No. W76412 for *Homo Sapiens* cDNA Clone Image:345098 (1996).
GenBank™ Accession No. AA130359 for *Homo Sapiens* cDNA Clone Image:503402 (1997).
GenBank™ Accession No. W81565 for *Homo Sapiens* cDNA Clone Image:347692 (1996).
GenBank™ Accession No. AA458753 for *Homo Sapiens* cDNA Clone Image:838296 (1998).
GenBank™ Accession No. AA826675 for *Homo Sapiens* cDNA Clone Image:1423064 (1998).
GenBank™ Accession No. W81612 for *Homo Sapiens* cDNA Clone Image:347692 (1996).
GenBank™ Accession No. T12258 for Heart *Homo Sapiens* cDNA Clone A478 (1994).
GenBank™ Accession No. AA056067 for *Homo Sapiens* cDNA Clone Image:377689 (1996).
GenBank™ Accession No. AA027306 for *Homo Sapiens* cDNA Clone Image:375487 (1997).
GenBank™ Accession No. AA026401 for *Homo Sapiens* cDNA Clone Image:375487 (1997).
GenBank™ Accession No. AA077342 for Chromosome 7 Fetal Brain cDNA Library *Homo Sapiens* cDNA clone 7B13G11 (1996).
GenBank™ Accession No. AA022531 for Soares Mouse NML *Mus Muscleus* cDNA Clone Image:364314 (1997).
GenBank™ Accession No. AA022530 for *Homo Sapiens* cDNA Clone Image:364315 (1997).
Copy of BlastN Search Using the MSP–5 Nucleic Acid Sequence (1996).
Copy of a TblastX Search Using the Translated MSP–5 Nucleic Acid Sequence (1996).
Schunkert, H., "Molecular Genetics of Congestive Heart Failure," Scand Cardoivasc J Suppl. 47:37–43, 1998.
Cohn, J., "Preventing Congestive Heart Failure", American Family Physician 57, No. 8 1901–1904, 1998.
Adams,M.D., "Initial Assesment of Human Gene Diversity and Expression Patterns Based Upon 83 Million Nucleotides of cDNA Sequence," Nature 377 (6547 Suppl), 3–174 (1995).
Liew, C.C., "A Catalogue of Genes in the Cardiovascular System as Identified by Expressed Sequence Tags," Proc. Natl. Acad. Sci. U.S.A. 91, p. 10645–10649 (1994).

* cited by examiner

MSP-5 NUCLEIC ACID SEQUENCE

GTCGACCCACGCGTCCGCTCGGCTGGATTTAAGGTTGCCGCTAGCCGCCTGG
GAATTTAAGGGACCCACACTACCTTCCCGAAGTTGAAGGCAAGCGGTGATTG
TTTGTAGACGGCGCTTTGTCATGGGACCTGTGCGGTTGGGAATATTGCTTTTC
CTTTTTTTGGCCGTGCACGAGGCTTGGGCTGGGATGTTGAAGGAGGAGGACG
ATGACACAGAACGCTTGCCCAGCAAATGCGAAGTGTGTAAGCTGCTGAGCAC
AGAGCTACAGGCGGAACTGAGTCGCACCGGTCGATCTCGAGAGGTGCTGGAG
CTGGGGCAGGTGCTGGATACAGGCAAGAGGAAGAGACACGTGCCTTACAGC
GTTTCAGAGACAAGGCTGGAAGAGGCCTTAGAGAATTTATGTGAGCGGATCC
TGGACTATAGTGTTCACGCTGAGCGCAAGGGCTCACTGAGATATGCCAAGGG
TCAGAGTCAGACCATGGCAACACTGAAAGGCCTAGTGCAGAAGGGGGTGAA
GGTGGATCTGGGGATCCCTCTGGAGCTTTGGGATGAGCCCAGCGTGGAGGTC
ACATACCTCAAGAAGCAGTGTGAGACCATGTTGGAGGAGTTTGAAGACATTG
TGGGAGACTGGTACTTCCACCATCAGGAGCAGCCCCTACAAAATTTTCTCTGT
GAAGGTCATGTGCTCCCAGCTGCTGAAACTGCATGTCTACAGGAAACTTGGA
CTGGAAAGGAGATCACAGATGGGGAAGAGAAAACAGAAGGGGAGGAAGAG
CAGGAGGAGGAGGAGGAAGAGGAGGAAGAGGAAGGGGGAGACAAGATGAC
CAAGACAGGAAGCCACCCCAAACTTGACCGAGAAGATCTTTGACCCTTGCCT
TTGAGCCCCCAGGAGGGGAAGGGATCATGGAGAGCCCTCTAAAGCCTGCACT
CTCCCTGCTCCACAGCTTTCAGGGTGTGTTTATGAGTGACTCCACCCAAGCTT
GTAGCTGTTCTCTCCCATCTAACCTCAGGCAAGATCCTGGTGAAACAGCATGA
CATGGCTTCTGGGGTGGAGGGTGGGGGTGGAGGTCCTGCTCCTAGAGATGAA
CTCTATCCAGCCCCTTAATTGGCAGGTGTATGTGCTGACAGTACTGAAAGCTT
TCCTCTTTAACTGATCCCACCCCCACCCAAAAGTCAGCAGTGGCACTGGAGCT
GTGGGCTTTGGGGAAGTCACTTAGCTCCTTAAGGTCTGTTTTAGACCCTTCC
AAGGAAGAGGCCAGAACGGACATTCTCTGCGATCTATATACATTGCCTGTAT
CCAGGAGGCTACACACCAGCAAACCGTGAAGGAGAATGGGACACTGGGTCA
TGGCCTGGAGTTGCTGATAATTTAGGTGGGATAGATACTTGGTCTACTTAAGC
TCAATGTAACCCAGAGCCCACCATATAGTTTTATAGGTGCTCAATTTTCTATA
TCGCTATTAAACTTTTTTCTTTTTTTCTAAAAAAAAAAAAAAAAGGGCGGCCG
C

MSP-5 AMINO ACID SEQUENCE

MGPVRLGILLFLFLAVHEAWAGMLKEEDDDTERLPSKCEVCKLLSTELQAELSR
TGRSREVLELGQVLDTGKRKRHVPYSVSETRLEEALENLCERILDYSVHAERKGS
LRYAKGQSQTMATLKGLVQKGVKVDLGIPLELWDEPSVEVTYLKKQCETMLEE
FEDIVGDWYFHHQEQPLQNFLCEGHVLPAAETACLQETWTGKEITDGEEKTEGE
EEQEEEEEEEEEGGDKMTKTGSHPKLDREDL.

FIGURE 1

MSP-5 NUCLEIC ACID MOLECULES AND USES THEREFOR

RELATED APPLICATIONS

This application claims priority to U.S. provisional Application No. 60/090,398, filed on Jun. 23, 1998, incorporated herein in its entirety by this reference.

BACKGROUND OF THE INVENTION

Congestive heart failure is a complex clinical syndrome characterized by exertional dyspnea, fatigue and, often, peripheral edema resulting from left ventricular dysfunction. The manifestation of congestive heart failure occurs secondary to a great variety of cardiac or systemic disorders that share a temporal or permanent loss of cardiac function. Recent progress in epidemiologic research has enabled the clear delineation of the predominant etiologic factors of congestive heart failure in Western societies. In particular, the long-term follow-up in the Framingham Heart Study has demonstrated that the majority of cases was predicted by one or more of four conditions: arterial hypertension, coronary artery disease, diabetes mellitus, and left ventricular hypertrophy (Levy D. et al. (1996) *JAMA* 275:1557–1562). In fact, the population attributable risk of these four factors combined accounted for about 90% of all cases with congestive heart failure.

Left ventricular hypertrophy as a complication of long-standing hypertension is a common factor in heart failure, even though the patient's blood pressure may be normal at the time congestive heart failure is diagnosed. In the absence of coronary artery disease and myocardial infarction, the left ventricular dysfunction in patients with hypertension often is predominantly a diastolic dysfunction with well-preserved chamber size and a normal ejection fraction.

Coronary artery disease is the most common etiology for left ventricular systolic dysfunction. Coronary artery disease (CAD) is a condition in which the heart muscle receives an inadequate amount of blood because of an interruption of its blood supply. It is presently the leading cause of death in the United States. Depending on the degree of interruption, symptoms can range from a mild chest pain to a full-scale heart attack. Generally, symptoms manifest when there is about a 75 percent narrowing of coronary artery lumina.

Stenotic and regurgitant valvular deformities, such as valvular stenosis, have also been well documented as contributing factors in ventricular dysfunction. Valvular stenosis is a narrowing, or stenosis, of one of the valves regulating blood flow in the heart. Stenosis may occur in the valve itself, most commonly in the mitral valve from rheumatic fever. All stenoses increase stress on the heart by making it work harder to push the blood through the abnormally narrow valve openings. As a result of mitral stenosis, blood pressure is increased. Angina pectoris and heart failure may accompany this disorder.

Finally, many diseases and toxins which directly affect the myocardium, can cause ventricular dysfunction. For example, excessive consumption of alcohol, diabetes mellitus and viral infections are associated with some causes of cardiomyopathy, whereas other cases may be genetic or idiopathic in nature.

SUMMARY OF THE INVENTION

The present invention is based, at least in part, on the discovery of novel nucleic acid molecules which encode proteins, referred to herein as "Myocardium Secreted Protein-5" ("MSP-5") proteins. The MSP-5 nucleic acid and protein molecules of the present invention are useful as modulating agents in regulating a variety of cellular processes, e.g., cardiac cellular processes. Accordingly, in one aspect, this invention provides isolated nucleic acid molecules encoding MSP-5 proteins or biologically active portions thereof, as well as nucleic acid fragments suitable as primers or hybridization probes for the detection of MSP-5-encoding nucleic acids.

In one embodiment, an MSP-5 nucleic acid molecule of the invention is at least 25%, 30%, 35%, 40%, 45%, 50%, 55%, 60%, 65%, 70%, 75%, 80%, 85%, 90%, 95% or more homologous to the nucleotide sequence (e.g., to the entire length of the nucleotide sequence) shown in SEQ ID NO:1, SEQ ID NO:3, or the nucleotide sequence of the DNA insert of the plasmid deposited with ATCC as Accession Number 209886, or a complement thereof. In a preferred embodiment, an MSP-5 nucleic acid molecule of the invention is at least 60% or more homologous to the nucleotide sequence (e.g., to the entire length of the nucleotide sequence) shown in SEQ ID NO:1, SEQ ID NO:3, or the nucleotide sequence of the DNA insert of the plasmid deposited with ATCC as Accession Number 209886, or a complement thereof. In a preferred embodiment, the isolated nucleic acid molecule has the nucleotide sequence shown SEQ ID NO:3, or a complement thereof. In another embodiment, the nucleic acid molecule further comprises nucleotides 1-54 of SEQ ID NO:1. In another embodiment, the nucleic acid molecule further comprises nucleotides 490–1512 of SEQ ID NO:1. In another preferred embodiment, the nucleic acid molecule has the nucleotide sequence shown in SEQ ID NO:1. In yet another preferred embodiment, an isolated nucleic acid molecule has the nucleotide sequence of the DNA insert of the plasmid deposited with ATCC as Accession Number 209886. In another preferred embodiment, the nucleic acid molecule comprises a fragment of at least 476 nucleotides of the nucleotide sequence of SEQ ID NO:1, SEQ ID NO:3, the DNA insert of the plasmid deposited with ATCC as Accession Number 209886, or a complement thereof.

In another embodiment, an MSP-5 nucleic acid molecule includes a nucleotide sequence encoding a protein having an amino acid sequence sufficiently homologous to the amino acid sequence of SEQ ID NO:2, SEQ ID NO:4, or an amino acid sequence encoded by the DNA insert of the plasmid deposited with ATCC as Accession Number 209886. In a preferred embodiment, an MSP-5 nucleic acid molecule includes a nucleotide sequence encoding a protein having an amino acid sequence at least 20%, 25%, 30%, 35%, 40%, 45%, 50%, 55%, 60%, 65%, 70%, 75%, 80%, 85%, 90%, 95% or more homologous to the amino acid sequence of SEQ ID NO:2 or SEQ ID NO:4 (e.g., the entire amino acid sequence of SEQ ID NO:2 or SEQ ID NO:4) or the amino acid sequence encoded by the DNA insert of the plasmid deposited with ATCC as Accession Number 209886. In another preferred embodiment, an isolated nucleic acid molecule encodes the amino acid sequence of human MSP-5. In yet another preferred embodiment, the nucleic acid molecule includes a nucleotide sequence encoding a protein having the amino acid sequence of SEQ ID NO:2, SEQ ID NO:4, or the amino acid sequence encoded by the DNA insert of the plasmid deposited with ATCC as Accession Number 209886.

In another embodiment, an isolated nucleic acid molecule of the present invention encodes a protein, preferably an MSP-5 protein, which includes a signal peptide.

Another embodiment of the invention features nucleic acid molecules, preferably MSP-5 nucleic acid molecules, which specifically detect MSP-5 nucleic acid molecules relative to nucleic acid molecules encoding non-MSP-5 proteins. For example, in one embodiment, such a nucleic acid molecule is at least 350, 400, 450, 476, 500, 550, 600, 650, 700, 750, or 800 nucleotides in length and hybridizes under stringent conditions to a nucleic acid molecule comprising the nucleotide sequence shown in SEQ ID NO:1, the nucleotide sequence of the DNA insert of the plasmid deposited with ATCC as Accession Number 209886, or a complement thereof. In a particularly preferred embodiment, the nucleic acid molecule comprises a fragment of at least 476 nucleotides of the nucleotide sequence of SEQ ID NO:1, SEQ ID NO:3, the DNA insert of the plasmid deposited with ATCC as Accession Number 209886, or a complement thereof. In preferred embodiments, the nucleic acid molecules are at least 15 (e.g., contiguous) nucleotides in length and hybridize under stringent conditions to nucleotides 1–46, 772–799, or 1509–1512 of SEQ ID NO:1. In other preferred embodiments, the nucleic acid molecules include nucleotides 1–46, 772–799, or 1509–1512 of SEQ ID NO:1.

In other preferred embodiments, the nucleic acid molecule encodes a naturally occurring allelic variant of a polypeptide which includes the amino acid sequence of SEQ ID NO:2, SEQ ID NO:4, or an amino acid sequence encoded by the DNA insert of the plasmid deposited with ATCC as Accession Number 209886, wherein the nucleic acid molecule hybridizes to a nucleic acid molecule which includes SEQ ID NO:1 or SEQ ID NO:3 under stringent conditions.

Another embodiment of the invention provides an isolated nucleic acid molecule which is antisense to an MSP-5 nucleic acid molecule, e.g., the coding strand of an MSP-5 nucleic acid molecule.

Another aspect of the invention provides a vector comprising an MSP-5 nucleic acid molecule. In certain embodiments, the vector is a recombinant expression vector. In another embodiment, the invention provides a host cell containing a vector of the invention. The invention also provides a method for producing a protein, preferably an MSP-5 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant MSP-5 proteins and polypeptides. In one embodiment, the isolated protein, preferably an MSP-5 protein, includes a signal peptide and is, preferably, secreted. In yet another embodiment, the isolated protein, preferably an MSP-5 protein, has an amino acid sequence sufficiently homologous to the amino acid sequence of SEQ ID NO:2 or SEQ ID NO:4. In a preferred embodiment, the protein, preferably an MSP-5 protein, has an amino acid sequence at least about 20%, 25%, 30%, 35%, 40%, 45%, 48%, 50%, 55%, 60%, 65%, 70%, 75%, 80%, 85%, 90%, 95% or more homologous to the amino acid sequence of SEQ ID NO:2 or SEQ ID NO:4 (e.g., the entire amino acid sequence of SEQ ID NO:2 or SEQ ID NO:4) or the amino acid sequence encoded by the DNA insert of the plasmid deposited with ATCC as Accession Number 209886. In another embodiment, the invention features fragments of the proteins having the amino acid sequence of SEQ ID NO:2 or SEQ ID NO:4 wherein the fragment comprises at least 15 amino acids (e.g., contiguous amino acids) of the amino acid sequence of SEQ ID NO:2 or SEQ ID NO:4, or an amino acid sequence encoded by the DNA insert of the plasmid deposited with the ATCC as Accession Number 209886. In another embodiment, the protein, preferably an MSP-5 protein, has the amino acid sequence of SEQ ID NO:2 or SEQ ID NO:4.

Another embodiment of the invention features an isolated protein, preferably an MSP-5 protein, which is encoded by a nucleic acid molecule having a nucleotide sequence at least about 25%, 30%, 35%, 40%, 45%, 50%, 55%, 60%, 65%, 70%, 75%, 80%, 85%, 90%, 95% or more homologous to the nucleotide sequence (e.g., to the entire length of the nucleotide sequence) of SEQ ID NO:1, SEQ ID NO:3, or a complement thereof. This invention further features an isolated protein, preferably an MSP-5 protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, or a complement thereof.

The proteins of the present invention or biologically active portions thereof, can be operatively linked to a non-MSP-5 polypeptide (e.g., heterologous amino acid sequences) to form fusion proteins. The invention further features antibodies, such as monoclonal or polyclonal antibodies, that specifically bind proteins of the invention, preferably MSP-5 proteins. In addition, the MSP-5 proteins or biologically active portions thereof can be incorporated into pharmaceutical compositions, which optionally include pharmaceutically acceptable carriers.

In another aspect, the present invention provides a method for detecting the presence of an MSP-5 nucleic acid molecule, protein or polypeptide in a biological sample by contacting the biological sample with an agent capable of detecting an MSP-5 nucleic acid molecule, protein or polypeptide such that the presence of an MSP-5 nucleic acid molecule, protein or polypeptide is detected in the biological sample.

In another aspect, the present invention provides a method for detecting the presence of MSP-5 activity in a biological sample by contacting the biological sample with an agent capable of detecting an indicator of MSP-5 activity such that the presence of MSP-5 activity is detected in the biological sample.

In another aspect, the invention provides a method for modulating MSP-5 activity comprising contacting a cell capable of expressing MSP-5 with an agent that modulates MSP-5 activity such that MSP-5 activity in the cell is modulated. In one embodiment, the agent inhibits MSP-5 activity. In another embodiment, the agent stimulates MSP-5 activity. In one embodiment, the agent is an antibody that specifically binds to an MSP-5 protein. In another embodiment, the agent modulates expression of MSP-5 by modulating transcription of an MSP-5 gene or translation of an MSP-5 mRNA. In yet another embodiment, the agent is a nucleic acid molecule having a nucleotide sequence that is antisense to the coding strand of an MSP-5 mRNA or an MSP-5 gene.

In one embodiment, the methods of the present invention are used to treat a subject having a disorder characterized by aberrant MSP-5 protein or nucleic acid expression or activity by administering an agent which is an MSP-5 modulator to the subject. In one embodiment, the MSP-5 modulator is an MSP-5 protein. In another embodiment the MSP-5 modulator is an MSP-5 nucleic acid molecule. In yet another embodiment, the MSP-5 modulator is a peptide, peptidomimetic, or other small molecule. In a preferred embodiment, the disorder characterized by aberrant MSP-5 protein or nucleic acid expression is a cardiovascular disorder, e.g., congestive heart failure.

The present invention also provides a diagnostic assay for identifying the presence or absence of a genetic alteration characterized by at least one of (i) aberrant modification or mutation of a gene encoding an MSP-5 protein; (ii) misregulation of the gene; and (iii) aberrant post-translational modification of an MSP-5 protein, wherein a wild-type form of the gene encodes a protein with an MSP-5 activity.

In another aspect the invention provides a method for identifying a compound that binds to or modulates the activity of an MSP-5 protein, by providing an indicator composition comprising an MSP-5 protein having MSP-5 activity, contacting the indicator composition with a test compound, and determining the effect of the test compound on MSP-5 activity in the indicator composition to identify a compound that modulates the activity of an MSP-5 protein.

Other features and advantages of the invention will be apparent from the following detailed description and claims.

BRIEF DESCRIPTION OF THE DRAWINGS

FIG. 1 depicts the cDNA sequence and predicted amino acid sequence of human MSP-5. The nucleotide sequence corresponds to nucleic acids 1 to 1512 of SEQ ID NO:1. The amino acid sequence corresponds to amino acids 1 to 248 of SEQ ID NO:2. The coding region without 5' and 3' untranslated regions of the human MSP-5 gene is shown in SEQ ID NO:3. The mature protein without the signal peptide sequence is shown in SEQ ID NO:4.

DETAILED DESCRIPTION OF THE INVENTION

The present invention is based, at least in part, on the discovery of novel molecules, referred to herein as MSP-5 nucleic acid and polypeptide molecules, which play a role in or function in a variety of cellular processes, e.g., cardiac cellular processes. In one embodiment, the MSP-5 molecules modulate the activity of one or more proteins involved in a cardiovascular disorder, e.g., congestive heart failure. In another embodiment, the MSP-5 molecules of the present invention are capable of modulating the transcription of genes involved in a cardiovascular disorder, e.g., congestive heart failure.

As used herein, the term "cardiovascular disorder" includes a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhytmias, and cardiomyopathies.

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies. Congestive heart failure is described in, for example, Cohn J. N. et al. (1998) *American Family Physician* 57:1901–04, the contents of which are incorporated herein by reference.

As used herein, the term "cardiac cellular processes" includes intra-cellular or inter-cellular processes involved in the functioning of the heart. Cellular processes involved in the nutrition and maintenance of the heart, the development of the heart, or the ability of the heart to pump blood to the rest of the body are intended to be covered by this term. Such processes include, for example, cardiac muscle contraction, distribution and transmission of electrical impulses, and cellular processes involved in the opening and closing of the cardiac valves. The term "cardiac cellular processes" further includes processes such as the transcription, translation and post-translational modification of proteins involved in the functioning of the heart, e.g., myofilament specific proteins, such as troponin I, troponin T, myosin light chain 1 (MLC1), and α-actinin.

The present invention is further based on the discovery of novel molecules, referred to herein as MSP-5 protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

In one embodiment of the invention, an MSP-5 protein contains at least one signal sequence. As used herein, a "signal sequence" refers to a peptide containing about 20 amino acids which occurs at the extreme N-terminal end of secretory and integral membrane proteins and in which at least 20%, more preferably at least 30%, and even more preferably at least 40% of the amino acid residues are hydrophobic. Such a "signal sequence", also referred to in the art as a "signal peptide", serves to direct a protein containing such a sequence to a lipid bilayer. For example, in one embodiment, an MSP-5 protein contains a signal sequence of about amino acids 1-22 of SEQ ID NO:2. The "signal sequence" is cleaved during processing of the mature protein. The mature MSP-5 protein corresponds to amino acids 23 to 248 of SEQ ID NO:2, shown separately as SEQ ID NO:4.

In a further embodiment, the invention features MSP-5 molecules which are secreted. As used herein, "secreted" refers to protein molecules which have the ability to be directed to the cellular plasma membrane (usually through a signal peptide) and subsequently released into the extracellular space. Such secreted MSP-5 molecules lack a trasmembrane domain.

Isolated proteins of the present invention, preferably MSP-5 proteins, have an amino acid sequence sufficiently homologous to the amino acid sequence of SEQ ID NO:2 or SEQ ID NO:4, or are encoded by a nucleotide sequence sufficiently homologous to SEQ ID NO:1 or SEQ ID NO:3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least about 50% homology, preferably about 60% homology, more preferably about 70%–80%, and even more preferably about 90–95% homology across the amino acid sequences of the domains and contain at least one and preferably two structural domains or motifs, are defined herein as sufficiently homologous. Furthermore, amino acid or nucleotide sequences which share at least about 50%, preferably about 60%, more preferably about 70–80%, or about 90–95% homology and share a common functional activity are defined herein as sufficiently homologous.

As used interchangeably herein an "MSP-5 activity", "biological activity of MSP-5" or "functional activity of MSP-5", refers to an activity exerted by an MSP-5 protein, polypeptide or nucleic acid molecule on an MSP-5 responsive cell as determined in vivo, or in vitro, according to standard techniques. In one embodiment, an MSP-5 activity is a direct activity, such as an association with a cell-surface protein (e.g., an MSP-5 receptor). In another embodiment, an MSP-5 activity is an indirect activity, such as the induction of transcription of a gene (e.g., a gene involved in cardiac function) mediated by interaction of the MSP-5 protein with a cell surface protein.

MSP-5 nucleic acid molecules were identified by screening a cDNA library prepared from a patient suffering from congestive heart failure (described in detail in Example 1). The human MSP-5 cDNA, which is approximately 1512 nucleotides in length (shown in SEQ ID NO:1), encodes a protein which is approximately 248 amino acid residues in length (shown in SEQ ID NO:2). The human MSP-5 protein is a secreted protein which further contains a signal sequence at about amino acids 1–22 of SEQ ID NO:2. The prediction of such a signal peptide can be made, for example, utilizing the computer algorithm SIGNALP (Henrik, et al. (1997) *Protein Engineering* 10:1–6).

The nucleotide sequence of the isolated human MSP-5 cDNA and the predicted amino acid sequence of the human MSP-5 polypeptide are shown in FIG. 1 and in SEQ ID NOs:1 and 2, respectively. A plasmid containing the full length nucleotide sequence encoding human MSP-5 was deposited with American Type Culture Collection (ATCC), 10801 University Blvd., Manassas, Va. 20110-2209, U.S.A. on May 20, 1998 and assigned Accession Number 209886. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The MSP-5 polypeptide, a biologically active portion or fragment of the polypeptide, or an allelic variant thereof can have one or more of the following MSP-5 activities: 1) it can interact with a non-MSP-5 protein molecule on the surface of the same cell (e.g., a cardiac cell) which secreted the MSP-5 protein molecule; 2) it can interact with a non-MSP-5 protein molecule on the surface of a different cell from that which secreted the MSP-5 protein molecule; 3) it can interact with (e.g., bind to) an MSP-5 receptor; 4) it can interact with (e.g., bind to) a non-MSP-5 receptor; 5) it can interact with (e.g., bind to) another protein in the extracellular milieu; 6) it can be secreted into the extracellular milieu; and 7) it can modulate the transcription of a gene involved in a cellular, e.g., cardiac, function.

Various aspects of the invention are described in further detail in the following subsections:

I. Isolated Nucleic Acid Molecules

One aspect of the invention pertains to isolated nucleic acid molecules that encode MSP-5 proteins or biologically active portions thereof, as well as nucleic acid fragments sufficient for use as hybridization probes to identify MSP-5-encoding nucleic acids (e.g., MSP-5 mRNA) and fragments for use as PCR primers for the amplification or mutation of MSP-5 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MSP-5 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, the nucleotide sequence of SEQ ID NO:3, or the nucleotide sequence of the DNA insert of the plasmid deposited with ATCC as Accession Number 209886, or a portion thereof, can be isolated using standard molecular biology techniques and the sequence information provided herein. Using all or portion of the nucleic acid sequence of SEQ ID NO:1, the nucleotide sequence of SEQ ID NO:3, or the nucleotide sequence of the DNA insert of the plasmid deposited with ATCC as Accession Number 209886, as a hybridization probe, MSP-5 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989).

Moreover, a nucleic acid molecule encompassing all or a portion of SEQ ID NO:1, SEQ ID NO:3, or the nucleotide sequence of the DNA insert of the plasmid deposited with ATCC as Accession Number 209886 can be isolated by the polymerase chain reaction (PCR) using synthetic oligonucleotide primers designed based upon the sequence of SEQ ID NO:1, SEQ ID NO:3, or the nucleotide sequence of the DNA insert of the plasmid deposited with ATCC as Accession Number 209886.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to MSP-5 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human MSP-5 cDNA. This cDNA comprises sequences encoding the human MSP-5 protein (i.e., "the coding region", from nucleotides 125–868), as well as 5' untranslated sequences (nucleotides 1–124) and 3' untranslated sequences (nucleotides 869–1512). Alternatively, the nucleic acid molecule can comprise only the coding region of SEQ ID NO:1 (e.g., nucleotides 125–868, corresponding to SEQ ID NO:3).

In another preferred embodiment, an isolated nucleic acid molecule of the invention comprises a nucleic acid molecule which is a complement of the nucleotide sequence shown in SEQ ID NO:1, SEQ ID NO:3, or the nucleotide sequence of the DNA insert of the plasmid deposited with ATCC as Accession Number 209886, or a portion of any of these nucleotide sequences. A nucleic acid molecule which is complementary to the nucleotide sequence shown in SEQ ID NO:1, SEQ ID NO:3, or the nucleotide sequence of the DNA insert of the plasmid deposited with ATCC as Accession Number 209886, is one which is sufficiently complementary to the nucleotide sequence shown in SEQ ID NO:1, SEQ ID NO:3, or the nucleotide sequence of the DNA insert of the plasmid deposited with ATCC as Accession Number 209886, such that it can hybridize to the nucleotide sequence shown in SEQ ID NO:1, SEQ ID NO:3, or the nucleotide sequence of the DNA insert of the plasmid deposited with ATCC as Accession Number 209886, thereby forming a stable duplex.

In still another preferred embodiment, an isolated nucleic acid molecule of the present invention comprises a nucleotide sequence which is at least about 25%, 30%, 35%, 40%, 45%, 50%, 55%, 60%, 65%, 70%, 75%, 80%, 85%, 90%, 95% or more homologous to the nucleotide sequence (e.g., to the entire length of the nucleotide sequence) shown in SEQ ID NO:1, SEQ ID NO:3, or the nucleotide sequence of the DNA insert of the plasmid deposited with ATCC as Accession Number 209886, or a portion of any of these nucleotide sequences.

Moreover, the nucleic acid molecule of the invention can comprise only a portion of the nucleic acid sequence of SEQ ID NO:1, SEQ ID NO:3, or the nucleotide sequence of the DNA insert of the plasmid deposited with ATCC as Accession Number 209886, for example a fragment which can be used as a probe or primer or a fragment encoding a biologically active portion of an MSP-5 protein. The nucleotide sequence determined from the cloning of the MSP-5 gene allows for the generation of probes and primers designed for use in identifying and/or cloning other MSP-5 family members, as well as MSP-5 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, or the nucleotide sequence of the DNA insert of the plasmid deposited with ATCC as Accession Number 209886, of an anti-sense sequence of SEQ ID NO:1, SEQ ID NO:3, or the nucleotide sequence of the DNA insert of the plasmid deposited with ATCC as Accession Number 209886, or of a naturally occurring allelic variant or mutant of SEQ ID NO:1, SEQ ID NO:3, or the nucleotide sequence of the DNA insert of the plasmid deposited with ATCC as Accession Number 209886. In an exemplary embodiment, a nucleic acid molecule of the present invention comprises a nucleotide sequence which is at least 350, 400, 450, 476, 500, 550, 600, 650, 700, 750, or 800 nucleotides in length and hybridizes under stringent hybridization conditions to a nucleic acid molecule of SEQ ID NO:1, SEQ ID NO:3, or the nucleotide sequence of the DNA insert of the plasmid deposited with ATCC as Accession Number 209886.

Probes based on the MSP-5 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress an MSP-5 protein, such as by measuring a level of an MSP-5-encoding nucleic acid in a sample of cells from a subject e.g., detecting MSP-5 mRNA levels or determining whether a genomic MSP-5 gene has been mutated or deleted.

A nucleic acid fragment encoding a "biologically active portion of an MSP-5 protein" can be prepared by isolating a portion of the nucleotide sequence of SEQ ID NO:1, SEQ ID NO:3, or the nucleotide sequence of the DNA insert of the plasmid deposited with ATCC as Accession Number 209886, which encodes a polypeptide having an MSP-5 biological activity (the biological activities of the MSP-5 proteins are described herein), expressing the encoded portion of the MSP-5 protein (e.g., by recombinant expression in vitro) and assessing the activity of the encoded portion of the MSP-5 protein.

The invention further encompasses nucleic acid molecules that differ from the nucleotide sequence shown in SEQ ID NO:1, SEQ ID NO:3, or the nucleotide sequence of the DNA insert of the plasmid deposited with ATCC as Accession Number 209886, due to the degeneracy of the genetic code and, thus, encode the same MSP-5 proteins as those encoded by the nucleotide sequence shown in SEQ ID NO:1, SEQ ID NO:3, or the nucleotide sequence of the DNA insert of the plasmid deposited with ATCC as Accession Number 209886. In another embodiment, an isolated nucleic acid molecule of the invention has a nucleotide sequence encoding a protein having an amino acid sequence shown in SEQ ID NO:2 or SEQ ID NO:4.

In addition to the MSP-5 nucleotide sequences shown in SEQ ID NO:1, SEQ ID NO:3, or the nucleotide sequence of the DNA insert of the plasmid deposited with ATCC as Accession Number 209886, it will be appreciated by those skilled in the art that DNA sequence polymorphisms that lead to changes in the amino acid sequences of the MSP-5 proteins may exist within a population (e.g., the human population). Such genetic polymorphism in the MSP-5 genes may exist among individuals within a population due to natural allelic variation. As used herein, the terms "gene" and "recombinant gene" refer to nucleic acid molecules which include an open reading frame encoding an MSP-5 protein, preferably a mammalian MSP-5 protein, and can further include non-coding regulatory sequences, and introns. Such natural allelic variations include both functional and non-functional MSP-5 proteins and can typically result in 1–5% variance in the nucleotide sequence of an MSP-5 gene. Any and all such nucleotide variations and resulting amino acid polymorphisms in MSP-5 genes that are the result of natural allelic variation and that do not alter the functional activity of an MSP-5 protein are intended to be within the scope of the invention.

Moreover, nucleic acid molecules encoding other MSP-5 family members and, thus, which have a nucleotide sequence which differs from the MSP-5 sequences of SEQ ID NO:1, SEQ ID NO:3, or the nucleotide sequence of the DNA insert of the plasmid deposited with ATCC as Accession Number 209886 are intended to be within the scope of the invention. For example, another MSP-5 cDNA can be identified based on the nucleotide sequence of human MSP-5. Moreover, nucleic acid molecules encoding MSP-5 proteins from different species, and thus which have a nucleotide sequence which differs from the MSP-5 sequences of SEQ ID NO:1, SEQ ID NO:3, or the nucleotide sequence of the DNA insert of the plasmid deposited with ATCC as Accession Number 209886 are intended to be within the scope of the invention. For example, a mouse MSP-5 cDNA can be identified based on the nucleotide sequence of a human MSP-5.

Nucleic acid molecules corresponding to natural allelic variants and homologues of the MSP-5 cDNAs of the invention can be isolated based on their homology to the MSP-5 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, or the nucleotide sequence of the DNA insert of the plasmid deposited with ATCC as Accession Number 209886. In other embodiment, the nucleic acid is at least 30, 50, 100, 150, 200, 250, 300, 350, 400, 450, 476, 500, 550, or 600 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology,* John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the MSP-5 sequences that may exist in the population, the skilled artisan will further appreciate that changes can be introduced by mutation into the nucleotide sequences of SEQ ID NO:1, SEQ ID NO:3, or the nucleotide sequence of the DNA insert of the plasmid deposited with ATCC as Accession Number 209886, thereby leading to changes in the amino acid sequence of the encoded MSP-5 proteins, without altering the functional ability of the MSP-5 proteins. For example, nucleotide substitutions leading to amino acid substitutions at "non-essential" amino acid residues can be made in the sequence of SEQ ID NO:1, SEQ ID NO:3, or the nucleotide sequence of the DNA insert of the plasmid deposited with ATCC as Accession Number 209886. A "non-essential" amino acid residue is a residue that can be altered from the wild-type sequence of MSP-5 (e.g., the sequence of SEQ ID NO:2 or SEQ ID NO:4) without altering the biological activity, whereas an "essential" amino acid residue is required for biological activity. For example, amino acid residues that are conserved among the MSP-5 proteins of the present invention, are predicted to be particularly unamenable to alteration. Furthermore, additional amino acid residues that are conserved between the MSP-5 proteins of the present invention and other MSP-5 family members are not likely to be amenable to alteration.

Accordingly, another aspect of the invention pertains to nucleic acid molecules encoding MSP-5 proteins that contain changes in amino acid residues that are not essential for activity. Such MSP-5 proteins differ in amino acid sequence from SEQ ID NO:2 or SEQ ID NO:4, yet retain biological activity. In one embodiment, the isolated nucleic acid molecule comprises a nucleotide sequence encoding a protein, wherein the protein comprises an amino acid sequence at least about 20%, 25%, 30%, 35%, 40%, 45%, 48%, 50%, 55%, 60%, 65%, 70%, 75%, 80%, 85%, 90%, 95% or more homologous to the amino acid sequence of SEQ ID NO:2 or SEQ ID NO:4 (e.g., the entire amino acid sequence of SEQ ID NO:2 or SEQ ID NO:4).

An isolated nucleic acid molecule encoding an MSP-5 protein homologous to the protein of SEQ ID NO:2 or SEQ ID NO:4 can be created by introducing one or more nucleotide substitutions, additions or deletions into the nucleotide sequence of SEQ ID NO:1, SEQ ID NO:3, or the nucleotide sequence of the DNA insert of the plasmid deposited with ATCC as Accession Number 209886, such that one or more amino acid substitutions, additions or deletions are introduced into the encoded protein. Mutations can be introduced into SEQ ID NO:1, SEQ ID NO:3, or the nucleotide sequence of the DNA insert of the plasmid deposited with ATCC as Accession Number 209886 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutaraic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an MSP-5 protein is preferably replaced with another amino acid residue from the same side chain family. Alternatively, in another embodiment, mutations can be introduced randomly along all or part of an MSP-5 coding sequence, such as by saturation mutagenesis, and the resultant mutants can be screened for MSP-5 biological activity to identify mutants that retain activity. Following mutagenesis of SEQ ID NO:1, SEQ ID NO:3, or the nucleotide sequence of the DNA insert of the plasmid deposited with ATCC as Accession Number 209886, the encoded protein can be expressed recombinantly and the activity of the protein can be determined.

In a preferred embodiment, a mutant MSP-5 protein can be assayed for the ability to: 1) interact with a non-MSP-5 protein molecule on the surface of the same cell (e.g., a cardiac cell) which secreted the MSP-5 protein molecule; 2) interact with a non-MSP-5 protein molecule on the surface of a different cell from that which secreted the MSP-5 protein molecule; 3) interact with (e.g., bind to) an MSP-5 receptor; 4) interact with (e.g., bind to) a non-MSP-5 receptor; 5) interact with (e.g., bind to) another protein in the extracellular milieu; 6) be secreted into the extracellular millieu; and 7) modulate the transcription of a gene involved in a cellular, e.g., cardiac, function.

In addition to the nucleic acid molecules encoding MSP-5 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire MSP-5 coding strand, or only to a portion thereof. In one embodiment, an antisense nucleic acid molecule is antisense to a "coding region" of the coding strand of a nucleotide sequence encoding MSP-5. The term "coding region" refers to the region of the nucleotide sequence comprising codons which are translated into amino acid residues (e.g., the coding region of human MSP-5 corresponds to SEQ ID NO:3). In another embodiment, the antisense nucleic acid molecule is antisense to a "noncoding region" of the coding strand of a nucleotide sequence encoding MSP-5. The term "noncoding region" refers to 5' and 3' sequences which flank the coding region that are not translated into amino acids (i.e., also referred to as 5' and 3' untranslated regions).

Given the coding strand sequences encoding MSP-5 disclosed herein (e.g., SEQ ID NO:3), antisense nucleic acids of the invention can be designed according to the rules of Watson and Crick base pairing. The antisense nucleic acid molecule can be complementary to the entire coding region of MSP-5 mRNA, but more preferably is an oligonucleotide which is antisense to only a portion of the coding or noncoding region of MSP-5 mRNA. For example, the antisense oligonucleotide can be complementary to the region surrounding the translation start site of MSP-5 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an MSP-5 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual βunits, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave MSP-5 mRNA transcripts to thereby inhibit translation of MSP-5 mRNA. A ribozyme having specificity for an MSP-5-encoding nucleic acid can be designed based upon the nucleotide sequence of an MSP-5 cDNA disclosed herein (i.e., SEQ ID NO:1, SEQ ID NO:3, or the nucleotide sequence of the DNA insert of the plasmid deposited with ATCC as Accession Number 209886). For example, a derivative of a Tetrahymena L-19 IVS RNA can be constructed in which the nucleotide sequence of the active site is complementary to the nucleotide sequence to be cleaved in an MSP-5-encoding mRNA. See, e.g., Cech et al. U.S. Pat. No. 4,987,071; and Cech et al. U.S. Pat. No. 5,116,742. Alternatively, MSP-5 mRNA can be used to select a catalytic RNA having a specific ribonuclease activity from a pool of RNA molecules. See, e.g., Bartel, D. and Szostak, J. W. (1993) *Science* 261:1411–1418.

Alternatively, MSP-5 gene expression can be inhibited by targeting nucleotide sequences complementary to the regulatory region of the MSP-5 (e.g., the MSP-5 promoter and/or enhancers) to form triple helical structures that prevent transcription of the MSP-5 gene in target cells. See generally, Helene, C. (1991) *Anticancer Drug Des.* 6(6) :569–84; Helene, C. et al. (1992) *Ann. N. Y. Acad. Sci.* 660:27–36; and Maher, L. J. (1992) *Bioassays* 14(12) :807–15.

In yet another embodiment, the MSP-5 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93:14670–675.

PNAs of MSP-5 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of MSP-5 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of MSP-5 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of MSP-5 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17:5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. U.S.* 86:6553–6556; Lemaitre et al. (1987) *Proc. Natl. Acad. Sci. U.S.A.* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated MSP-5 Proteins and Anti-MSP-5 Antibodies

One aspect of the invention pertains to isolated MSP-5 proteins, and biologically active portions thereof, as well as polypeptide fragments suitable for use as immunogens to raise anti-MSP-5 antibodies. In one embodiment, native MSP-5 proteins can be isolated from cells or tissue sources by an appropriate purification scheme using standard protein purification techniques. In another embodiment, MSP-5 proteins are produced by recombinant DNA techniques. Alternative to recombinant expression, an MSP-5 protein or polypeptide can be synthesized chemically using standard peptide synthesis techniques.

An "isolated" or "purified" protein or biologically active portion thereof is substantially free of cellular material or other contaminating proteins from the cell or tissue source from which the MSP-5 protein is derived, or substantially free from chemical precursors or other chemicals when chemically synthesized. The language "substantially free of cellular material" includes preparations of MSP-5 protein in which the protein is separated from cellular components of the cells from which it is isolated or recombinantly produced. In one embodiment, the language "substantially free of cellular material" includes preparations of MSP-5 protein having less than about 30% (by dry weight) of non-MSP-5 protein (also referred to herein as a "contaminating protein"), more preferably less than about 20% of non-MSP-5 protein, still more preferably less than about 10% of non-MSP-5 protein, and most preferably less than about 5% non-MSP-5 protein. When the MSP-5 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of MSP-5 protein in which the protein is separated from chemical precursors or other chemicals which are involved in the synthesis of the protein. In one embodiment, the language "substantially free of chemical precursors or other chemicals" includes preparations of MSP-5 protein having less than about 30% (by dry weight) of chemical precursors or non-MSP-5 chemicals, more preferably less than about 20% chemical precursors or non-MSP-5 chemicals, still more preferably less than about 10% chemical precursors or non-MSP-5 chemicals, and most preferably less than about 5% chemical precursors or non-MSP-5 chemicals.

Biologically active portions of an MSP-5 protein include peptides comprising amino acid sequences sufficiently homologous to or derived from the amino acid sequence of the MSP-5 protein, e.g., the amino acid sequence shown in SEQ ID NO:2 or SEQ ID NO:4, which include less amino acids than the full length MSP-5 proteins, and exhibit at least one activity of an MSP-5 protein. Typically, biologically active portions comprise a domain or motif with at least one activity of the MSP-5 protein. A biologically active portion of an MSP-5 protein can be a polypeptide which is, for example, at least 10, 25, 50, 100 or more amino acids in length.

In a preferred embodiment, the MSP-5 protein has an amino acid sequence shown in SEQ ID NO:2 or SEQ ID NO:4. In other embodiments, the MSP-5 protein is substantially homologous to SEQ ID NO:2 or SEQ ID NO:4, and retains the functional activity of the protein of SEQ ID NO:2 or SEQ ID NO:4, yet differs in amino acid sequence due to natural allelic variation or mutagenesis, as described in detail in subsection I above. Accordingly, in another embodiment, the MSP-5 protein is a protein which comprises an amino acid sequence at least about 20%, 25%, 30%, 35%, 40%, 45%, 48%, 50%, 55%, 60%, 65%, 70%, 75%, 80%, 85%, 90%, 95% or more homologous to the amino acid sequence of SEQ ID NO:2 or SEQ ID NO:4 (e.g., the entire amino acid sequence of SEQ ID NO:2 or SEQ ID NO:4).

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the MSP-5 amino acid sequence of SEQ ID NO:2 or SEQ ID NO:4 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to MSP-5 nucleic acid molecules of the invention. BLAST protein searches can be performed with the XBLAST program, score=50, wordlength=3 to obtain amino acid sequences homologous to MSP-5 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides MSP-5 chimeric or fusion proteins. As used herein, an MSP-5 "chimeric protein" or "fusion protein" comprises an MSP-5 polypeptide operatively linked to a non-MSP-5 polypeptide. An "MSP-5 polypeptide" refers to a polypeptide having an amino acid sequence corresponding to MSP-5, whereas a "non-MSP-5 polypeptide" refers to a polypeptide having an amino acid sequence corresponding to a protein which is not substantially homologous to the MSP-5 protein, e.g., a protein which is different from the MSP-5 protein and which is derived from the same or a different organism. Within an MSP-5 fusion protein the MSP-5 polypeptide can correspond to all or a portion of an MSP-5 protein. In a preferred embodiment, an MSP-5 fusion protein comprises at least one biologically active portion of an MSP-5 protein. In another preferred embodiment, an MSP-5 fusion protein comprises at least two biologically active portions of an MSP-5 protein. Within the fusion protein, the term "operatively linked" is intended to indicate that the MSP-5 polypeptide and the non-MSP-5 polypeptide are fused in-frame to each other. The non-MSP-5 polypeptide can be fused to the N-terminus or C-terminus of the MSP-5 polypeptide.

For example, in one embodiment, the fusion protein is a GST-MSP-5 fusion protein in which the MSP-5 sequences are fused to the C-terminus of the GST sequences. Such fusion proteins can facilitate the purification of recombinant MSP-5.

In another embodiment, the fusion protein is an MSP-5 protein containing a heterologous signal sequence at its N-terminus. For example, the native MSP-5 signal sequence (i.e, about amino acids 1 to 22 of SEQ ID NO:2) can be removed and replaced with a signal sequence from another protein. In certain host cells (e.g., mammalian host cells), expression and/or secretion of MSP-5 can be increased through use of a heterologous signal sequence.

The MSP-5 fusion proteins of the invention can be incorporated into pharmaceutical compositions and administered to a subject in vivo. The MSP-5 fusion proteins can be used to affect the bioavailability of an MSP-5 substrate. Use of MSP-5 fusion proteins may be useful therapeutically for the treatment of cardiovascular disorders, e.g., congestive heart failure. Moreover, the MSP-5-fusion proteins of the invention can be used as immunogens to produce anti-MSP-5 antibodies in a subject, to purify MSP-5 ligands and in screening assays to identify molecules which inhibit the interaction of MSP-5 with an MSP-5 substrate.

Preferably, an MSP-5 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An MSP-5-encoding nucleic acid can be cloned into such an expression vector such that the fusion moiety is linked in-frame to the MSP-5 protein.

The present invention also pertains to variants of the MSP-5 proteins which function as either MSP-5 agonists (mimetics) or as MSP-5 antagonists. Variants of the MSP-5 proteins can be generated by mutagenesis, e.g., discrete point mutation or truncation of an MSP-5 protein. An agonist of the MSP-5 proteins can retain substantially the same, or a subset, of the biological activities of the naturally occurring form of an MSP-5 protein. An antagonist of an MSP-5 protein can inhibit one or more of the activities of the naturally occurring form of the MSP-5 protein by, for example, competitively modulating a cardiovascular system activity of an MSP-5 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the MSP-5 protein.

In one embodiment, variants of an MSP-5 protein which function as either MSP-5 agonists (mimetics) or as MSP-5 antagonists can be identified by screening combinatorial libraries of mutants, e.g., truncation mutants, of an MSP-5 protein for MSP-5 protein agonist or antagonist activity. In one embodiment, a variegated library of MSP-5 variants is generated by combinatorial mutagenesis at the nucleic acid level and is encoded by a variegated gene library. A variegated library of MSP-5 variants can be produced by, for example, enzymatically ligating a mixture of synthetic oligonucleotides into gene sequences such that a degenerate set of potential MSP-5 sequences is expressible as individual polypeptides, or alternatively, as a set of larger fusion proteins (e.g., for phage display) containing the set of MSP-5 sequences therein. There are a variety of methods which can be used to produce libraries of potential MSP-5 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MSP-5 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an MSP-5 protein coding sequence can be used to generate a variegated population of MSP-5 fragments for screening and subsequent selection of variants of an MSP-5 protein. In one embodiment, a library of coding sequence fragments can be generated by treating a double stranded PCR fragment of an MSP-5 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the MSP-5 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MSP-5 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify MSP-5 variants (Arkin and Yourvan (1992) *Proc. Natl. Acad. Sci. U.S.A.* 89:7811–7815; Delgrave et al. (1993) *Protein Engineering* 6(3):327–331).

In one embodiment, cell based assays can be exploited to analyze a variegated MSP-5 library. For example, a library of expression vectors can be transfected into a cell line which ordinarily synthesizes and secretes MSP-5. The transfected cells are then cultured such that MSP-5 and a particular mutant MSP-5 are secreted and the effect of expression of the mutant on MSP-5 activity in cell supernatants can be detected, e.g., by any of a number of enzymatic assays. Plasmid DNA can then be recovered from the cells which score for inhibition, or alternatively, potentiation of MSP-5 activity, and the individual clones further characterized.

An isolated MSP-5 protein, or a portion or fragment thereof, can be used as an immunogen to generate antibodies that bind MSP-5 using standard techniques for polyclonal and monoclonal antibody preparation. A full-length MSP-5 protein can be used or, alternatively, the invention provides antigenic peptide fragments of MSP-5 for use as immunogens. The antigenic peptide of MSP-5 comprises at least 8 amino acid residues of the amino acid sequence shown in SEQ ID NO:2 or SEQ ID NO:4 and encompasses an epitope of MSP-5 such that an antibody raised against the peptide forms a specific immune complex with MSP-5. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of MSP-5 that are located on the surface of the protein, e.g., hydrophilic regions.

An MSP-5 immunogen typically is used to prepare antibodies by immunizing a suitable subject, (e.g., rabbit, goat, mouse or other mammal) with the immunogen. An appropriate immunogenic preparation can contain, for example, recombinantly expressed MSP-5 protein or a chemically synthesized MSP-5 polypeptide. The preparation can further include an adjuvant, such as Freund's complete or incomplete adjuvant, or similar immunostimulatory agent. Immunization of a suitable subject with an immunogenic MSP-5 preparation induces a polyclonal anti-MSP-5 antibody response.

Accordingly, another aspect of the invention pertains to anti-MSP-5 antibodies. The term "antibody" as used herein refers to immunoglobulin molecules and immunologically active portions of immunoglobulin molecules, i.e., molecules that contain an antigen binding site which specifically binds (immunoreacts with) an antigen, such as MSP-5. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind MSP-5. The term "monoclonal antibody" or "monoclonal antibody composition", as used herein, refers to a population of antibody molecules that contain only one species of an antigen binding site capable of immunoreacting with a particular epitope of MSP-5. A monoclonal antibody composition thus typically displays a single binding affinity for a particular MSP-5 protein with which it immunoreacts.

Polyclonal anti-MSP-5 antibodies can be prepared as described above by immunizing a suitable subject with an MSP-5 immunogen. The anti-MSP-5 antibody titer in the immunized subject can be monitored over time by standard techniques, such as with an enzyme linked immunosorbent assay (ELISA) using immobilized MSP-5. If desired, the antibody molecules directed against MSP-5 can be isolated from the mammal (e.g., from the blood) and further purified by well known techniques, such as protein A chromatography to obtain the IgG fraction. At an appropriate time after immunization, e.g., when the anti-MSP-5 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. U.S.A.* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an MSP-5 immunogen as described above, and the culture supernatants of the resulting hybridoma cells are screened to identify a hybridoma producing a monoclonal antibody that binds MSP-5.

Any of the many well known protocols used for fusing lymphocytes and immortalized cell lines can be applied for the purpose of generating an anti-MSP-5 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies,* cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind MSP-5, e.g., using a standard ELISA assay.

Alternative to preparing monoclonal antibody-secreting hybridomas, a monoclonal anti-MSP-5 antibody can be identified and isolated by screening a recombinant combinatorial immunoglobulin library (e.g., an antibody phage display library) with MSP-5 to thereby isolate immunoglobulin library members that bind MSP-5. Kits for generating and screening phage display libraries are commercially available (e.g., the Pharmacia *Recombinant Phage Antibody System,* Catalog No. 27-9400-01; and the Stratagene *SurfZAP*™ *Phage Display Kit,* Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology*

9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. U.S.A.* 89:3576–3580; Garrad et al. (1991) *Bio/Technology* 9:1373–1377; Hoogenboom et al. (1991) Nuc. Acid Res. 19:4133–4137; Barbas et al. (1991) *Proc. Natl. Acad. Sci. U.S.A.* 88:7978–7982; and McCafferty et al. *Nature* (1990) 348:552–554.

Additionally, recombinant anti-MSP-5 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European patent application 184,187; Taniguchi, M., European patent application 171, 496; Morrison et al. European patent application 173,494; Neuberger et al. PCT International Publication No. WO 86/01533; Cabilly et al. U.S. Pat. No. 4,816,567; Cabilly et al. European patent application 125,023; Better et al. (1988) *Science* 240:1041–1043; Liu et al. (1987) *Proc. Natl. Acad. Sci. U.S.A.* 84:3439–3443; Liu et al. (1987) *J. Immunol.* 139:3521–3526; Sun et al. (1987) *Proc. Natl. Acad. Sci. U.S.A.* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No, 5,225, 539; Jones et al. (1986) *Nature* 321:552–525; Verhoeyan et al. (1988) *Science* 239:1534; and Beidler et al. (1988) *J. Immunol.* 141:4053–4060.

An anti-MSP-5 antibody (e.g., monoclonal antibody) can be used to isolate MSP-5 by standard techniques, such as affinity chromatography or immunoprecipitation. An anti-MSP-5 antibody can facilitate the purification of natural MSP-5 from cells and of recombinantly produced MSP-5 expressed in host cells. Moreover, an anti-MSP-5 antibody can be used to detect MSP-5 protein (e.g., in a cellular lysate or cell supernatant) in order to evaluate the abundance and pattern of expression of the MSP-5 protein. Anti-MSP-5 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding an MSP-5 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., MSP-5 proteins, mutant forms of MSP-5 proteins, fusion proteins, and the like).

The recombinant expression vectors of the invention can be designed for expression of MSP-5 proteins in prokaryotic or eukaryotic cells. For example, MSP-5 proteins can be expressed in bacterial cells such as *E. coli,* insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in MSP-5 activity assays, (e.g., direct assays or competitive assays described in detail below), or to generate antibodies specific for MSP-5 proteins, for example. In a preferred embodiment, an MSP-5 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the MSP-5 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, MSP-5 proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. U.S.A.* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MSP-5 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews-Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an MSP-5 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an MSP-5 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an MSP-5 protein. Accordingly, the invention further provides methods for producing an MSP-5 protein using the host cells of the invention. In one embodiment, the method comprises culturing the host cell of invention (into which a recombinant expression vector encoding an MSP-5 protein has been introduced) in a suitable medium such that an MSP-5 protein is produced. In another embodiment, the method further comprises isolating an MSP-5 protein from the medium or the host cell.

The host cells of the invention can also be used to produce non-human transgenic animals. For example, in one embodiment, a host cell of the invention is a fertilized oocyte or an embryonic stem cell into which MSP-5-coding sequences have been introduced. Such host cells can then be used to create non-human transgenic animals in which exogenous MSP-5 sequences have been introduced into their genome or homologous recombinant animals in which endogenous MSP-5 sequences have been altered. Such animals are useful for studying the function and/or activity of an MSP-5 and for identifying and/or evaluating modulators of MSP-5 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous MSP-5 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an MSP-5-encoding nucleic acid into the male pronuclei of a fertilized oocyte, e.g., by microinjection, retroviral infection, and allowing the oocyte to develop in a pseudopregnant female foster animal. The MSP-5 cDNA sequence of SEQ ID NO:1 can be introduced as a transgene into the genome of a non-human animal. Alternatively, a nonhuman homologue of a human MSP-5 gene, such as a mouse or rat MSP-5 gene, can be used as a transgene. Alternatively, an MSP-5 gene homologue, such as another MSP-5 family member, can be isolated based on hybridization to the MSP-5 cDNA sequences of SEQ ID NO:1, SEQ ID NO:3, or the DNA insert of the plasmid deposited with ATCC as Accession Number 209886 (described further in subsection I above) and used as a transgene. Intronic sequences and polyadenylation signals can also be included in the transgene to increase the efficiency of expression of the transgene. A tissue-specific regulatory sequencers) can be operably linked to an MSP-5 transgene to direct expression of an MSP-5 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of an MSP-5 transgene in its genome and/or expression of MSP-5 mRNA in tissues or cells of the animals. A transgenic founder animal can then be used to breed additional animals carrying the transgene. Moreover, transgenic animals carrying a transgene encoding an MSP-5 protein can further be bred to other transgenic animals carrying other transgenes.

To create a homologous recombinant animal, a vector is prepared which contains at least a portion of an MSP-5 gene into which a deletion, addition or substitution has been introduced to thereby alter, e.g., functionally disrupt, the MSP-5 gene. The MSP-5 gene can be a human gene (e.g., the cDNA of SEQ ID NO:1), but more preferably, is a non-human homologue of a human MSP-5 gene (e.g., a cDNA isolated by stringent hybridization with the nucleotide sequence of SEQ ID NO:1). For example, a mouse MSP-5 gene can be used to construct a homologous recombination vector suitable for altering an endogenous MSP-5 gene in the mouse genome. In a preferred embodiment, the vector is designed such that, upon homologous recombination, the endogenous MSP-5 gene is functionally disrupted (i.e., no longer encodes a functional protein; also referred to as a "knock out" vector). Alternatively, the vector can be designed such that, upon homologous recombination, the endogenous MSP-5 gene is mutated or otherwise altered but still encodes a functional protein (e.g., the upstream regulatory region can be altered to thereby alter the expression of the endogenous MSP-5 protein). In the homologous recombination vector, the altered portion of the MSP-5 gene is flanked at its 5' and 3' ends by additional nucleic acid sequence of the MSP-5 gene to allow for homologous recombination to occur between the exogenous MSP-5 gene carried by the vector and an endogenous MSP-5 gene in an embryonic stem cell. The additional flanking MSP-5 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced MSP-5 gene has homologously recombined with the endogenous MSP-5 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, trasgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. U.S.A.* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The MSP-5 nucleic acid molecules, MSP-5 proteins, and anti-MSP-5 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an MSP-5 protein or anti-MSP-5 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. U.S.A.* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express MSP-5 protein (e.g., via a recombinant expression vector in a host cell in gene therapy applications), to detect MSP-5 mRNA (e.g., in a biological sample) or a genetic alteration in an MSP-5 gene, and to modulate MSP-5 activity, as described further below. The MSP-5 proteins can be used to treat disorders characterized by insufficient or excessive production of an MSP-5 substrate or production of MSP-5 inhibitors. In addition, the MSP-5 proteins can be used to screen for naturally occurring MSP-5 substrates, to screen for drugs or compounds which modulate MSP-5 activity, as well as to treat disorders characterized by insufficient or excessive production of MSP-5 protein or production of MSP-5 protein forms which have decreased or aberrant activity compared to MSP-5 wild type protein. Moreover, the anti-MSP-5 antibodies of the invention can be used to detect and isolate MSP-5 proteins, regulate the bioavailability of MSP-5 proteins, and modulate MSP-5 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to MSP-5 proteins, have a stimulatory or inhibitory effect on, for example, MSP-5 expression or MSP-5 activity, or have a stimulatory or inhibitory effect on, for example, the expression or activity of MSP-5 substrate.

In one embodiment, the invention provides assays for screening candidate or test compounds which are substrates of an MSP-5 protein or polypeptide or biologically active portion thereof. In another embodiment, the invention provides assays for screening candidate or test compounds which bind to or modulate the activity of an MSP-5 protein or polypeptide or biologically active portion thereof, e.g., modulate the ability of MSP-5 to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. U.S.A.* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci U.S.A.* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an MSP-5 protein or biologically active portion thereof is contacted with a test compound and the ability of the test compound to modulate MSP-5 activity determined. The cell, for example, can be of mammalian origin, e.g., a cell which expresses an MSP-5 cognate receptor, or a yeast cell. Determining the ability of the test compound to modulate MSP-5 activity can be accomplished, for example, by coupling the MSP-5 molecule with a radioisotope or enzymatic label such that binding of the MSP-5 molecule to its cognate receptor can be determined by detecting the labeled MSP-5 molecule in a complex. For example, MSP-5 molecules, e.g., MSP-5 proteins, can be labeled with $^{125}I$, $^{35}S$, $^{14}C$, or $^{3}H$, either directly or indirectly, and the radioisotope detected by direct counting of radioemission or by scintillation counting. Alternatively, MSP-5 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between MSP-5 and its cognate receptor, without the labeling of any of the interactants. For example, a microphysiometer can be used to detect the interaction of MSP-5 with its cognate receptor without the labeling of either MSP-5 or the receptor. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, the assay comprises contacting a cell which is responsive to an MSP-5 protein or biologically active portion thereof, with an MSP-5 protein or biologically-active portion thereof, to form an assay mixture, contacting the assay mixture with a test compound, and determining the ability of the test compound to modulate the activity of the MSP-5 protein or biologically active portion thereof, wherein determining the ability of the test compound to modulate the activity of the MSP-5 protein or biologically active portion thereof comprises determining the ability of the test compound to modulate a biological activity of the MSP-5-responsive cell (e.g., determining the ability of the test compound to modulate the expression of MSP-5 regulated genes).

In another embodiment, an assay is a cell-based assay comprising contacting a cell expressing an MSP-5 target molecule (e.g., an MSP-5 receptor) with a test compound and determining the ability of the test compound to modulate (e.g. stimulate or inhibit) the activity of the MSP-5 target molecule. Determining the ability of the test compound to modulate the activity of an MSP-5 target molecule can be accomplished, for example, by determining the ability of the MSP-5 protein to bind to or interact with the MSP-5 target molecule.

Determining the ability of the MSP-5 protein to bind to or interact with an MSP-5 target molecule can be accomplished by one of the methods described above for determining direct binding. In a preferred embodiment, determining the ability of the MSP-5 protein to bind to or interact with an MSP-5 target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which an MSP-5 protein or biologically active portion thereof is contacted with a test compound and the ability of the test compound to bind to the MSP-5 protein or biologically active portion thereof is determined. Binding of the test compound to the MSP-5 protein can be determined either directly or indirectly as described above. In a preferred embodiment, the assay includes contacting the MSP-5 protein or biologically active portion thereof with a known compound which binds MSP-5 to form an assay mixture, contacting the assay mixture with a test compound, and determining the ability of the test compound to interact with an MSP-5 protein, wherein determining the ability of the test compound to interact with an MSP-5 protein comprises determining the ability of the test compound to preferentially bind to MSP-5 or biologically active portion thereof as compared to the known compound.

In another embodiment, the assay is a cell-free assay in which an MSP-5 protein or biologically active portion thereof is contacted with a test compound and the ability of the test compound to modulate (e.g., stimulate or inhibit) the activity of the MSP-5 protein or biologically active portion thereof is determined. Determining the ability of the test compound to modulate the activity of an MSP-5 protein can be accomplished, for example, by determining the ability of the MSP-5 protein to bind to an MSP-5 target molecule by one of the methods described above for determining direct binding. Determining the ability of the MSP-5 protein to bind to an MSP-5 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an MSP-5 protein can be accomplished by determining the ability of the MSP-5 protein to further modulate the activity of a downstream effector (e.g., an MSP-5 mediated signal transduction pathway component) of an MSP-5 target molecule (e.g., an MSP-5 receptor). For example, the activity of the effector molecule on an appropriate target can be determined, or the binding of the effector to an appropriate target can be determined as previously described.

In yet another embodiment, the cell-free assay involves contacting an MSP-5 protein or biologically active portion thereof with a known compound which binds the MSP-5 protein to form an assay mixture, contacting the assay mixture with a test compound, and determining the ability of the test compound to interact with the MSP-5 protein, wherein determining the ability of the test compound to interact with the MSP-5 protein comprises determining the ability of the MSP-5 protein to preferentially bind to or modulate the activity of an MSP-5 target molecule.

The cell-free assays of the present invention are amenable to use of both soluble and/or membrane-bound forms of proteins (e.g., MSP-5 proteins or biologically active portions thereof, or receptors to which MSP-5 binds). In the case of cell-free assays in which a membrane-bound form a protein is used (e.g., a cell surface MSP-5 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-l100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either MSP-5 or its target molecule to facilitate separation of complexed from uncomplexed forms of one or both of the proteins, as well as to accommodate automation of the assay. Binding of a test compound to an MSP-5 protein, or interaction of an MSP-5 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ MSP-5 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or MSP-5 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of MSP-5 binding or activity determined using standard techniques.

Other techniques for immobilizing proteins on matrices can also be used in the screening assays of the invention. For example, either an MSP-5 protein or an MSP-5 target molecule can be immobilized utilizing conjugation of biotin and streptavidin. Biotinylated MSP-5 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with MSP-5 protein or target molecules but which do not interfere with binding of the MSP-5 protein to its target molecule can be derivatized to the wells of the plate, and unbound target or MSP-5 protein trapped in the wells by antibody conjugation. Methods for detecting such complexes, in addition to those described above for the GST-immobilized complexes, include immunodetection of complexes using antibodies reactive with the MSP-5 protein or target molecule, as well as enzyme-linked assays which rely on detecting an enzymatic activity associated with the MSP-5 protein or target molecule.

In another embodiment, modulators of MSP-5 expression are identified in a method wherein a cell is contacted with a candidate compound and the expression of MSP-5 mRNA or protein in the cell is determined. The level of expression of MSP-5 mRNA or protein in the presence of the candidate compound is compared to the level of expression of MSP-5 mRNA or protein in the absence of the candidate compound. The candidate compound can then be identified as a modulator of MSP-5 expression based on this comparison. For example, when expression of MSP-5 mRNA or protein is greater (statistically significantly greater) in the presence of the candidate compound than in its absence, the candidate compound is identified as a stimulator of MSP-5 mRNA or protein expression. Alternatively, when expression of MSP-5 mRNA or protein is less (statistically significantly less) in the presence of the candidate compound than in its absence, the candidate compound is identified as an inhibitor of MSP-5 mRNA or protein expression. The level of MSP-5 mRNA or protein expression in the cells can be determined by methods described herein for detecting MSP-5 mRNA or protein.

In yet another aspect of the invention, the MSP-5 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with MSP-5 ("MSP-5-binding proteins" or "MSP-5-bp") and are involved in MSP-5 activity. Such MSP-5-binding proteins are also likely to be involved in the propagation of signals by the MSP-5 proteins or MSP-5 targets as, for example, downstream elements of an MSP-5-mediated signaling pathway. Alternatively, such MSP-5-binding proteins are likely to be MSP-5 inhibitors.

The two-hybrid system is based on the modular nature of most transcription factors, which consist of separable DNA-binding and activation domains. Briefly, the assay utilizes two different DNA constructs. In one construct, the gene that codes for an MSP-5 protein is fused to a gene encoding the DNA binding domain of a known transcription factor (e.g., GAL-4). In the other construct, a DNA sequence, from a library of DNA sequences, that encodes an unidentified protein ("prey" or "sample" is fused to a gene that codes for the activation domain of the known transcription factor. If the "bait" and the "prey" proteins are able to interact, in vivo, forming an MSP-5-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the MSP-5 protein.

This invention further pertains to novel agents identified by the above-described screening assays. Accordingly, it is within the scope of this invention to further use an agent identified as described herein in an appropriate animal model. For example, an agent identified as described herein (e.g., an MSP-5 modulating agent, an antisense MSP-5 nucleic acid molecule, an MSP-5-specific antibody, or an MSP-5-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the MSP-5 nucleotide sequences, described herein, can be used to map the location of the MSP-5 genes on a chromosome. The mapping of the MSP-5 sequences to chromosomes is an important first step in correlating these sequences with genes associated with disease.

Briefly, MSP-5 genes can be mapped to chromosomes by preparing PCR primers (preferably 15–25 bp in length) from the MSP-5 nucleotide sequences. Computer analysis of the MSP-5 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the MSP-5 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the MSP-5 nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *Proc. Natl. Acad. Sci. U.S.A.*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the MSP-5 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The MSP-5 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the MSP-5 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The MSP-5 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from MSP-5 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial MSP-5 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the MSP-5 nucleotide sequences or portions thereof, e.g., fragments derived from the noncoding regions of SEQ ID NO:1, having a length of at least 20 bases, preferably at least 30 bases.

The MSP-5 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such MSP-5 probes can be used to identify tissue by species and/or by organ type.

In a similar fashion, these reagents, e.g., MSP-5 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining MSP-5 protein and/or nucleic acid expression as well as MSP-5 activity, in the context of a biological sample (e.g., blood, serum, cells, tissue) to thereby determine whether an individual is afflicted with a disease or disorder, or is at risk of developing a disorder, associated with aberrant MSP-5 expression or activity. The invention also provides for prognostic (or predictive) assays for determining whether an individual is at risk of developing a disorder associated with MSP-5 protein, nucleic acid expression or activity. For example, mutations in an MSP-5 gene can be assayed in a biological sample. Such assays can be used for prognostic or predictive purpose to thereby phophylactically treat an individual prior to the onset of a disorder characterized by or associated with MSP-5 protein, nucleic acid expression or activity.

Another aspect of the invention pertains to monitoring the influence of agents (e.g., drugs, compounds) on the expression or activity of MSP-5 in clinical trials.

These and other agents are described in further detail in the following sections.

1. Diagnostic Assays

An exemplary method for detecting the presence or absence of MSP-5 protein or nucleic acid in a biological sample involves obtaining a biological sample from a test subject and contacting the biological sample with a compound or an agent capable of detecting MSP-5 protein or nucleic acid (e.g., mRNA, genomic DNA) that encodes MSP-5 protein such that the presence of MSP-5 protein or nucleic acid is detected in the biological sample. A preferred agent for detecting MSP-5 mRNA or genomic DNA is a labeled nucleic acid probe capable of hybridizing to MSP-5 mRNA or genomic DNA. The nucleic acid probe can be, for example, a full-length MSP-5 nucleic acid, such as the nucleic acid of SEQ ID NO:1 (or that of SEQ ID NO:3, or the DNA insert of the plasmid deposited with ATCC as Accession Number 209886, or a portion thereof), such as an oligonucleotide of at least 15, 30, 50, 100, 250 or 500 nucleotides in length and sufficient to specifically hybridize under stringent conditions to MSP-5 mRNA or genomic DNA. Other suitable probes for use in the diagnostic assays of the invention are described herein.

A preferred agent for detecting MSP-5 protein is an antibody capable of binding to MSP-5 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect MSP-5 mRNA, protein, or genomic DNA in a biological sample in vitro as well as in vivo. For example, in vitro techniques for detection of MSP-5 mRNA include Northern hybridizations and in situ hybridizations. In vitro techniques for detection of MSP-5 protein include enzyme linked immunosorbent assays (ELISAs), Western blots, immunoprecipitations and immunofluorescence. In vitro techniques for detection of MSP-5 genomic DNA include Southern hybridizations. Furthermore, in vivo techniques for detection of MSP-5 protein include introducing into a subject a labeled anti-MSP-5 antibody- For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting MSP-5 protein, mRNA, or genomic DNA, such that the presence of MSP-5 protein, mRNA or genomic DNA is detected in the biological sample, and comparing the presence of MSP-5 protein, mRNA or genomic DNA in the control sample with the presence of MSP-5 protein, mRNA or genomic DNA in the test sample.

The invention also encompasses kits for detecting the presence of MSP-5 in a biological sample. For example, the kit can comprise a labeled compound or agent capable of detecting MSP-5 protein or mRNA in a biological sample; means for determining the amount of MSP-5 in the sample; and means for comparing the amount of MSP-5 in the sample with a standard. The compound or agent can be packaged in a suitable container. The kit can further comprise instructions for using the kit to detect MSP-5 protein or nucleic acid.

2. Prognostic Assays

The diagnostic methods described herein can furthermore be utilized to identify subjects having or at risk of developing a disease or disorder associated with aberrant MSP-5 expression or activity. For example, the assays described herein, such as the preceding diagnostic assays or the following assays, can be utilized to identify a subject having or at risk of developing a disorder associated with MSP-5 protein, nucleic acid expression or activity. Thus, the present invention provides a method for identifying a disease or disorder associated with aberrant MSP-5 expression or activity in which a test sample is obtained from a subject and MSP-5 protein or nucleic acid (e.g., mRNA, genomic DNA) is detected, wherein the presence of MSP-5 protein or nucleic acid is diagnostic for a subject having or at risk of developing a disease or disorder associated with aberrant MSP-5 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant MSP-5 expression or activity. Thus, the present invention provides methods for determining whether a subject can be effectively treated with an agent for a disorder associated with aberrant MSP-5 expression or activity in which a test sample is obtained and MSP-5 protein or nucleic acid expression or activity is detected (e.g., wherein the abundance of MSP-5 protein or nucleic acid expression or activity is diagnostic for a subject that can be administered the agent to treat a disorder associated with aberrant MSP-5 expression or activity).

The methods of the invention can also be used to detect genetic alterations in an MSP-5 gene, thereby determining if a subject with the altered gene is at risk for a disorder associated with the MSP-5 gene. In preferred embodiments, the methods include detecting, in a sample of cells from the subject, the presence or absence of a genetic alteration characterized by at least one of an alteration affecting the integrity of a gene encoding an MSP-5-protein, or the mis-expression of the MSP-5 gene. For example, such genetic alterations can be detected by ascertaining the existence of at least one of 1) a deletion of one or more nucleotides from an MSP-5 gene; 2) an addition of one or more nucleotides to an MSP-5 gene; 3) a substitution of one or more nucleotides of an MSP-5 gene, 4) a chromosomal rearrangement of an MSP-5 gene; 5) an alteration in the level of a messenger RNA transcript of an MSP-5 gene, 6) aberrant modification of an MSP-5 gene, such as of the methylation pattern of the genomic DNA, 7) the presence of a non-wild type splicing pattern of a messenger RNA transcript of an MSP-5 gene, 8) a non-wild type level of an MSP-5-protein, 9) allelic loss of an MSP-5 gene, and 10) inappropriate post-translational modification of an MSP-5-protein. As described herein, there are a large number of assay techniques known in the art which can be used for detecting alterations in an MSP-5 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. U.S.A.* 91:360–364), the latter of which can be particularly useful for detecting point mutations in the MSP-5-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an MSP-5 gene under conditions such that hybridization and amplification of the MSP-5-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. U.S.A.* 87:1874–1878), transcriptional amplification system (Kwoh, D. Y. et al., (1989) *Proc. Natl. Acad. Sci. U.S.A.* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an MSP-5 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in MSP-5 can be identified by hybridizing a sample and control nucleic acids, e.g., DNA or RNA, to high density arrays containing hundreds or thousands of oligonucleotides probes (Cronin, M. T. et al. (1996) *Human Mutation* 7:244–255; Kozal, M. J. et al. (1996) *Nature Medicine* 2:753–759). For example, genetic mutations in MSP-5 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the MSP-5 gene and detect mutations by comparing the sequence of the sample MSP-5 with the corresponding wild-type (control) sequence. Examples of sequencing reactions include those based on techniques developed by Maxim and Gilbert ((1977) *Proc. Natl. Acad. Sci. U.S.A.* 74:560) or Sanger ((1977) *Proc. Natl. Acad. Sci. U.S.A.* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the MSP-5 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type MSP-5 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci U.S.A.* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in MSP-5 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an MSP-5 sequence, e.g., a wild-type MSP-5 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in MSP-5 genes. For example, single strand conformation polymorphism (SSCP) may be used to detect differences in electrophoretic mobility between mutant and wild type nucleic acids (Orita et al. (1989) *Proc Natl. Acad. Sci U.S.A.*: 86:2766, see also Cotton (1993) *Mutat Res* 285:125–144; and Hayashi (1992) *Genet Anal Tech Appl* 9:73–79). Single-stranded DNA fragments of sample and control MSP-5 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad Sci U.S.A.* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci U.S.A.* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an MSP-5 gene.

Furthermore, any cell type or tissue in which MSP-5 is expressed may be utilized in the prognostic assays described herein.

3. Monitoring of Effects During Clinical Trials

Monitoring the influence of agents (e.g., drugs or compounds) on the expression or activity of an MSP-5 protein can be applied not only in basic drug screening, but also in clinical trials. For example, the effectiveness of an agent determined by a screening assay as described herein to increase MSP-5 gene expression, protein levels, or upregulate MSP-5 activity, can be monitored in clinical trials of subjects exhibiting decreased MSP-5 gene expression, protein levels, or downregulated MSP-5 activity. Alternatively, the effectiveness of an agent determined by a screening assay to decrease MSP-5 gene expression, protein levels, or downregulate MSP-5 activity, can be monitored in clinical trials of subjects exhibiting increased MSP-5 gene expression, protein levels, or upregulated MSP-5 activity. In such clinical trials, the expression or activity of an MSP-5 gene, and preferably, other genes that have been implicated in a disorder can be used as a "read out" or markers of the phenotype of a particular cell.

For example, and not by way of limitation, genes, including MSP-5, that are modulated in cells by treatment with an agent (e.g., compound, drug or small molecule) which modulates MSP-5 activity (e.g., identified in a screening assay as described herein) can be identified. Thus, to study the effect of agents on an MSP-5 associated disorder, for example, in a clinical trial, cells can be isolated and RNA prepared and analyzed for the levels of expression of MSP-5 and other genes implicated in the MSP-5 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of MSP-5 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of an MSP-5 protein, mRNA, or genomic DNA in the pre-administration sample; (iii) obtaining one or more post-administration samples from the subject; (iv) detecting the level of expression or activity of the MSP-5 protein, mRNA, or genomic DNA in the post-administration samples; (v) comparing the level of expression or activity of the MSP-5 protein, mRNA, or genomic DNA in the pre-administration sample with the MSP-5 protein, mRNA, or genomic DNA in the post administration sample or samples; and (vi) altering the administration of the agent to the subject accordingly. For example, increased administration of the agent may be desirable to increase the expression or activity of MSP-5 to higher levels than detected, i.e., to increase the effectiveness of the agent. Alternatively, decreased administration of the agent may be desirable to decrease expression or activity of MSP-5 to lower levels than detected, i.e. to decrease the effectiveness of the agent. According to such an embodiment, MSP-5 expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant MSP-5 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the MSP-5 molecules of the present invention or MSP-5 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant MSP-5 expression or activity, by administering to the subject an MSP-5 or an agent which modulates MSP-5 expression or at least one MSP-5 activity. Subjects at risk for a disease which is caused or contributed to by aberrant MSP-5 expression or activity can be identified by, for example, any or a combination of diagnostic or prognostic assays as described herein. Administration of a prophylactic agent can occur prior to the manifestation of symptoms characteristic of the MSP-5 aberrancy, such that a disease or disorder is prevented or, alternatively, delayed in its progression. Depending on the type of MSP-5 aberrancy, for example, an MSP-5, MSP-5 agonist or MSP-5 antagonist agent can be used for treating the subject. The appropriate agent can be determined based on screening assays described herein.

2. Therapeutic Methods

Another aspect of the invention pertains to methods of modulating MSP-5 expression or activity for therapeutic purposes. Accordingly, in an exemplary embodiment, the modulatory method of the invention involves contacting a cell with an MSP-5 or agent that modulates one or more of the activities of MSP-5 protein activity associated with the cell. An agent that modulates MSP-5 protein activity can be an agent as described herein, such as a nucleic acid or a protein, a naturally-occurring target molecule of an MSP-5 protein (e.g., an MSP-5 receptor), an MSP-5 antibody, an MSP-5 agonist or antagonist, a peptidomimetic of an MSP-5 agonist or antagonist, or other small molecule. In one embodiment, the agent stimulates one or more MSP-5 activities. Examples of such stimulatory agents include active MSP-5 protein and a nucleic acid molecule encoding MSP-5 that has been introduced into the cell. In another embodiment, the agent inhibits one or more MSP-5 activities. Examples of such inhibitory agents include antisense MSP-5 nucleic acid molecules, anti-MSP-5 antibodies, and MSP-5 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an MSP-5 protein or nucleic acid molecule. In one embodiment, the method involves administering an agent (e.g., an agent identified by a screening assay described herein), or combination of agents that modulates (e.g., upregulates or downregulates) MSP-5 expression or activity. In another embodiment, the method involves administering an MSP-5 protein or nucleic acid molecule as therapy to compensate for reduced or aberrant MSP-5 expression or activity.

Stimulation of MSP-5 activity is desirable in situations in which MSP-5 is abnormally downregulated and/or in which increased MSP-5 activity is likely to have a beneficial effect. For example, stimulation of MSP-5 activity is desirable in situations in which an MSP-5 is downregulated and/or in which increased MSP-5 activity is likely to have a beneficial effect. Likewise, inhibition of MSP-5 activity is desirable in situations in which MSP-5 is abnormally upregulated and/or in which decreased MSP-5 activity is likely to have a beneficial effect.

3. Pharmacopenomics

The MSP-5 molecules of the present invention, as well as agents, or modulators which have a stimulatory or inhibitory effect on MSP-5 activity (e.g., MSP-5 gene expression) as identified by a screening assay described herein can be administered to individuals to treat (prophylactically or therapeutically) disorders (e.g., cardiovascular disorders such as congestive heart failure) associated with aberrant MSP-5 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an MSP-5 molecule or MSP-5 modulator as well as tailoring the dosage and/or therapeutic regimen of treatment with an MSP-5 molecule or MSP-5 modulator.

Pharmacogenomics deals with clinically significant hereditary variations in the response to drugs due to altered drug disposition and abnormal action in affected persons. See e.g., Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., an MSP-5 protein or MSP-5 receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an MSP-5 molecule or MSP-5 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an MSP-5 molecule or MSP-5 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

IDENTIFICATION AND CHARACTERIZATION OF HUMAN MSP-5 cDNA

In this example, the identification and characterization of the gene encoding human MSP-5 is described.

Isolation of the human MSP-5 cDNA

The invention is based, at least in part, on the discovery of a human gene encoding a novel protein, referred to herein as MSP-5. The human MSP-5 was isolated from a cDNA library which was prepared from tissue obtained from a subject suffering from congestive heart failure. Briefly, a cardiac tissue sample was obtained from a biopsy of a 42 year old woman suffering from congestive heart failure. mRNA was isolated from the cardiac tissue and a cDNA library was prepared therefrom using art known methods (described in, for example, *Molecular Cloning A Laboratory Manual*, 2nd Ed., ed. by Sambrook, Fritsch and Maniatis (Cold Spring Harbor Laboratory Press: 1989). Using a program which identifies the presence of signal peptides (Nielsen, H. et al. (1997) *Protein Engineering* 10:1–6) a positive clone was isolated.

The sequence of the entire clone was determined and found to contain an open reading frame of 248 amino acids termed "Myocardium Secreted Protein -5" or MSP-5. Signal peptide algorithms predict that MSP-5 contains a signal peptide (amino acids 1-22 of SEQ ID NO:2). Cleavage of the putative signal peptide would result in the secretion of a 226 amino acid protein with a predicted molecular weight of approximately 26 kilodaltons (kD).

The nucleotide sequence encoding the human MSP-5 protein is shown in FIG. 1 and is set forth as SEQ ID NO:1. The full length protein encoded by this nucleic acid comprises about 248 amino acids and has the amino acid sequence shown in FIG. 1 and set forth as SEQ ID NO:2. The coding region (open reading frame) of SEQ ID NO:1 is set forth as SEQ ID NO:3. The clone comprising the entire coding region of human MSP-5 was deposited with the American Type Culture Collection (ATCC®), Rockville, Md., on May 20, 1998, and assigned Accession No. 209886.

Analysis of Human MSP-5

A BLAST search (Altschul et al. (1990) *J. Mol. Biol.* 215:403) of the nucleotide and protein sequences of human MSP-5 revealed that MSP-5 is similar to the following proteins: C. elegans C11H1.7 protein (Accession No. Z70205) and human CTG4a (Accession No. U80744). These proteins are approximately 40% identical (over MSP-5 amino acids 91–132) and 48% identical (over MSP-5 amino acids 27-65) to MSP-5, respectively, at the amino acid level.

Tissue Distribution of MSP-5 mRNA

This Example describes the tissue distribution of MSP-5 mRNA, as determined by Northern blot hybridization.

Northern blot hybridizations with the various RNA samples were performed under standard conditions and washed under stringent conditions, i.e., 0.2×SSC at 65° C. A DNA probe corresponding to the coding region of MSP-5 (SEQ ID NO:3) was used. The DNA was radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) were probed in ExpressHyb hybridization solution (Clontech) and washed at high stringency according to manufacturer's recommendations.

MSP-5 message was detected in every tissue tested. However, the MSP-5 message was most prominent in heart, brain, placenta, fetal lung, liver, kidney, testis, small intestine, and pituitary gland.

Example 2

EXPRESSION OF RECOMBINANT MSP-5 PROTEIN IN BACTERIAL CELLS

In this example, MSP-5 is expressed as a recombinant glutathione-S-transferase (GST) fusion polypeptide in *E. coli* and the fusion polypeptide is isolated and characterized. Specifically, MSP-5 is fused to GST and this fusion polypeptide is expressed in *E. coli*, e.g., strain PEB199. As the human MSP-5 protein is predicted to be approximately 26 kDa, and GST is predicted to be 26 kDa, the fusion polypeptide is predicted to be approximately 52 kDa, in molecular weight. Expression of the GST-MSP-5 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

EXPRESSION OF RECOMBINANT MSP-5 PROTEIN IN COS CELLS

To express the MSP-5 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire MSP-5 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the MSP-5 DNA sequence is amplified by PCR using two primers. The 5' primer contains the restriction site of interest followed by approximately twenty nucleotides of the MSP-5 coding sequence starting from the initiation codon; the 3' end sequence contains complementary sequences to the other restriction site of interest, a translation stop codon, the HA tag or FLAG tag and the last 20 nucleotides of the MSP-5 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the MSP-5 gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the MSP-5-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the MSP-5 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1%

NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the MSP-5 coding sequence is cloned directly into the polylinker of the pCDNA/Amp vector using the appropriate restriction sites. The resulting plasmid is transfected into COS cells in the manner described above, and the expression of the MSP-5 polypeptide is detected by radiolabelling and immunoprecipitation using an MSP-5 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising the nucleotide sequence set forth in SEQ ID NO:1, or a full complement thereof.

2. An isolated nucleic acid molecule comprising the nucleotide sequence set forth in SEQ ID NO:3, or a full complement thereof.

3. An isolated nucleic acid molecule consisting of the nucleotide sequence set forth in SEQ ID NO:1, or a full complement thereof.

4. An isolated nucleic acid molecule consisting of the nucleotide sequence set forth in SEQ ID NO:3, or a full complement thereof.

5. An isolated nucleic acid molecule which encodes a polypeptide comprising the amino acid sequence set forth in SEQ ID NO:2, or a full complement thereof.

6. An isolated nucleic acid molecule which encodes a polypeptide consisting of the amino acid sequence set forth in SEQ ID NO:2, or a full complement thereof.

7. An isolated nucleic acid molecule which encodes a polypeptide consisting of the amino acid sequence set forth in SEQ ID NO:4, or a full complement thereof.

8. An isolated nucleic acid molecule which encodes a polypeptide comprising the amino acid sequence set forth in SEQ ID NO:4, or a full complement thereof.

9. Deleted and American Type Culture Collection inserted.

10. Deleted and inserted Myocardium Secreted Protein-5 (MSP-5).

11. An isolated nucleic acid molecule which encodes a naturally occurring allelic variant of a polypeptide having an MSP-5 activity, comprising the amino acid sequence of SEQ ID NO:2 or SEQ ID NO:4, wherein the nucleic acid molecule hybridizes to a nucleic acid molecule consisting of SEQ ID NO:1 or SEQ ID NO:3 at 6×SSC at 45° C., followed by one or more washes in 0.2×SSC, 0.1% SDS at 65° C.

12. An isolated nucleic acid molecule comprising a nucleotide sequence which is at least 90% identical to the nucleotide sequence of SEQ ID NO:1 or SEQ ID NO:3, or a full complement thereof.

13. An isolated nucleic acid molecule consisting of a nucleotide sequence which is at least 90% identical to the nucleotide sequence of SEQ ID NO:1 or SEQ ID NO:3, or a full complement thereof.

14. An isolated nucleic acid molecule encoding a polypeptide comprising an amino acid sequence at least 90% identical to the amino acid sequence of SEQ ID NO:2 or SEQ ID NO:4.

15. An isolated nucleic acid molecule encoding a polypeptide consisting of an amino acid sequence at least 90% identical to the amino acid sequence of SEQ ID NO:2 or SEQ ID NO:4.

16. An isolated nucleic acid molecule comprising the nucleic acid molecule of claim 1, and a nucleotide sequence encoding a beterologous polypeptide.

17. A vector comprising the nucleic acid molecule of claim 1.

18. The vector of claim 17, which is an expression vector.

19. A vector comprising the nucleic acid molecule of claim 2.

20. The vector of claim 19, which is an expression vector.

21. A vector comprising the nucleic acid molecule of claim 3.

22. The vector of claim 21, which is an expression vector.

23. A vector comprising the nucleic acid molecule of claim 4.

24. The vector of claim 23, which is an expression vector.

25. A vector comprising the nucleic acid molecule of claim 5.

26. The vector of claim 25, which is an expression vector.

27. A vector comprising the nucleic acid molecule of claim 6.

28. The vector of claim 27, which is an expression vector.

29. A vector comprising the nucleic acid molecule of claim 7.

30. The vector of claim 29, which is an expression vector.

31. A vector comprising the nucleic acid molecule of claim 8.

32. The vector of claim 31, which is an expression vector.

33. A vector comprising the nucleic acid molecule of claim 9.

34. The vector of claim 33, which is an expression vector.

35. A vector comprising the nucleic acid molecule of claim 10.

36. The vector of claim 35, which is an expression vector.

37. A vector comprising the nucleic acid molecule of claim 11.

38. The vector of claim 37, which is an expression vector.

39. A vector comprising the nucleic acid molecule of claim 12.

40. The vector of claim 39, which is an expression vector.

41. A vector comprising the nucleic acid molecule of claim 13.

42. The vector of claim 41, which is an expression vector.

43. A vector comprising the nucleic acid molecule of claim 14.

44. The vector of claim 43, which is an expression vector.

45. A vector comprising the nucleic acid molecule of claim 15.

46. The vector of claim 45, which is an expression vector.

47. An isolated nucleic acid molecule comprising the nucleic acid molecule of claim 2, and a nucleotide sequence encoding a heterologous polypeptide.

48. An isolated nucleic acid molecule comprising the nucleic acid molecule of claim 3, and a nucleotide sequence encoding a heterologous polypeptide.

49. An isolated nucleic acid molecule comprising the nucleic acid molecule of claim 4; and a nucleotide sequence encoding a heterologous polypeptide.

50. An isolated nucleic acid molecule comprising the nucleic acid molecule of claim 5, and a nucleotide sequence encoding a heterologous polypeptide.

51. An isolated nucleic acid molecule comprising the nucleic acid molecule of claim 6, and a nucleotide sequence encoding a heterologous polypeptide.

52. An isolated nucleic acid molecule comprising the nucleic acid molecule of claim 7, and a nucleotide sequence encoding a heterologous polypeptide.

53. An isolated nucleic acid molecule comprising the nucleic acid molecule of claim 8, and a nucleotide sequence encoding a heterologous polypeptide.

54. An isolated nucleic acid molecule comprising the nucleic acid molecule of claim 9, and a nucleotide sequence encoding a heterologous polypeptide.

55. An isolated nucleic acid molecule comprising the nucleic acid molecule of claim 10, and a nucleotide sequence encoding a heterologous polypeptide.

56. An isolated nucleic acid molecule comprising the nucleic acid molecule of claim 11, and a nucleotide sequence encoding a heterologous polypeptide.

57. An isolated nucleic acid molecule comprising the nucleic acid molecule of claim 12, and a nucleotide sequence encoding a heterologous polypeptide.

58. An isolated nucleic acid molecule comprising the nucleic acid molecule of claim 13, and a nucleotide sequence encoding a heterologous polypeptide.

59. An isolated nucleic acid molecule comprising the nucleic acid molecule of claim 14, and a nucleotide sequence encoding a heterologous polypeptide.

60. An isolated nucleic acid molecule comprising the nucleic acid molecule of claim 15, and a nucleotide sequence encoding a heterologous polypeptide.

61. A kit comprising the nucleic acid molecule of claim 1 and instructions for use.

62. A kit comprising the nucleic acid molecule of claim 2 and instructions for use.

63. A kit comprising the nucleic acid molecule of claim 3 and instructions for use.

64. A kit comprising the nucleic acid molecule of claim 4 and instructions for use.

65. A kit comprising the nucleic acid molecule of claim 5 and instructions for use.

66. A kit comprising the nucleic acid molecule of claim 6 and instructions for use.

67. A kit comprising the nucleic acid molecule of claim 7 and instructions for use.

68. A kit comprising the nucleic acid molecule of claim 8 and instructions for use.

69. A kit comprising the nucleic acid molecule of claim 9 and instructions for use.

70. A kit comprising the nucleic acid molecule of claim 10 and instructions for use.

71. A kit comprising the nucleic acid molecule of claim 11 and instructions for use.

72. A kit comprising the nucleic acid molecule of claim 12 and instructions for use.

73. A kit comprising the nucleic acid molecule of claim 13 and instructions for use.

74. A kit comprising the nucleic acid molecule of claim 14 and instructions for use.

75. A kit comprising the nucleic acid molecule of claim 15 and instructions for use.

76. A recombinant host cell comprising the nucleic acid molecule of claim 1 operatively linked to a recombinant regulatory sequence.

77. A recombinant host cell comprising the nucleic acid molecule of claim 2 operatively linked to a recombinant regulatory sequence.

78. A recombinant host cell comprising the nucleic acid molecule of claim 3 operatively linked to a recombinant regulatory sequence.

79. A recombinant host cell comprising the nucleic acid molecule of claim 4 operatively linked to a recombinant regulatory sequence.

80. A recombinant host cell comprising the nucleic acid molecule of claim 5 operatively linked to a recombinant regulatory sequence.

81. A recombinant host cell comprising the nucleic acid molecule of claim 6 operatively linked to a recombinant regulatory sequence.

82. A recombinant host cell comprising the nucleic acid molecule of claim 7 operatively linked to a recombinant regulatory sequence.

83. A recombinant host cell comprising the nucleic acid molecule of claim 8 operatively linked to a recombinant regulatory sequence.

84. A recombinant host cell comprising the nucleic acid molecule of claim 9 operatively linked to a recombinant regulatory sequence.

85. A recombinant host cell comprising the nucleic acid molecule of claim 10 operatively linked to a recombinant regulatory sequence.

86. A recombinant host cell comprising the nucleic acid molecule of claim 11 operatively linked to a recombinant regulatory sequence.

87. A recombinant host cell comprising the nucleic acid molecule of claim 12 operatively linked to a recombinant regulatory sequence.

88. A recombinant host cell comprising the nucleic acid molecule of claim 13 operatively linked to a recombinant regulatory sequence.

89. A recombinant host cell comprising the nucleic acid molecule of claim 14 operatively linked to a recombinant regulatory sequence.

90. A recombinant host cell comprising the nucleic acid molecule of claim 15 operatively linked to a recombinant regulatory sequence.

91. A method of expressing a polypeptide comprising the step of culturing the host cell of any one of claims 76–89, or 90 under conditions in which the nucleic acid molecule is expressed, thereby expressing the polypeptide.

92. A method of producing a polypeptide comprising the step of culturing the host cell of any one of claims 76–89, or 90 under conditions in which the nucleic acid molecule is expressed.

* * * * *

UNITED STATES PATENT AND TRADEMARK OFFICE
CERTIFICATE OF CORRECTION

PATENT NO. : 6,204,013 B1
DATED : March 20, 2001
INVENTOR(S) : Khodadoust Mehran It is certified that error appears in the above-identified patent and that said Letters Patent is hereby corrected as shown below:

Claim 9,
Delete "Deleted and American Type Culture Collection inserted" and insert "An isolated nucleic acid molecule comprising the nucleotide sequence contained in the plasmid deposited with American Type Culture Collection as Accession Number 209886, or a full complement thereof".

Claim 10,
Delete "Deleted and inserted Myocardium Secreted Protein-5 (MSP-5)" and insert "An isolated nucleic acid molecule which encodes a polypeptide having a Myocardium Secreted Protein-5 (MSP-5) activity, wherein the nucleic acid molecule hybridizes to a nucleic acid molecule consisting of SEQ ID NO:1 or SEQ ID NO:3 at 6X SSC at 45°C, followed by one or more washes in 0.2X SSC, 0.1% SDS at 65°C".

Claim 49,
Line 2, delete "4;" and insert "4,".

Signed and Sealed this

Twentieth Day of November, 2001

*Attest:*

NICHOLAS P. GODICI
*Attesting Officer*    Acting Director of the United States Patent and Trademark Office

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1512 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 125..868

(xi) SEQUENCE DESCRIPTION: SEQ ID NO:1:

```
GTCGACCCAC GCGTCCGCTC GGCTGGATTT AAGGTTGCCG CTAGCCGCCT GGGAATTTAA        60

GGGACCCACA CTACCTTCCC GAAGTTGAAG GCAAGCGGTG ATTGTTTGTA GACGGCGCTT       120

TGTC ATG GGA CCT GTG CGG TTG GGA ATA TTG CTT TTC CTT TTT TTG GCC       169
     Met Gly Pro Val Arg Leu Gly Ile Leu Leu Phe Leu Phe Leu Ala
       1               5                  10                  15

GTG CAC GAG GCT TGG GCT GGG ATG TTG AAG GAG GAG GAC GAT GAC ACA        217
Val His Glu Ala Trp Ala Gly Met Leu Lys Glu Glu Asp Asp Asp Thr
                 20                  25                  30

GAA CGC TTG CCC AGC AAA TGC GAA GTG TGT AAG CTG CTG AGC ACA GAG        265
Glu Arg Leu Pro Ser Lys Cys Glu Val Cys Lys Leu Leu Ser Thr Glu
             35                  40                  45

CTA CAG GCG GAA CTG AGT CGC ACC GGT CGA TCT CGA GAG GTG CTG GAG        313
Leu Gln Ala Glu Leu Ser Arg Thr Gly Arg Ser Arg Glu Val Leu Glu
         50                  55                  60

CTG GGG CAG GTG CTG GAT ACA GGC AAG AGG AAG AGA CAC GTG CCT TAC        361
Leu Gly Gln Val Leu Asp Thr Gly Lys Arg Lys Arg His Val Pro Tyr
     65                  70                  75

AGC GTT TCA GAG ACA AGG CTG GAA GAG GCC TTA GAG AAT TTA TGT GAG        409
Ser Val Ser Glu Thr Arg Leu Glu Glu Ala Leu Glu Asn Leu Cys Glu
 80                  85                  90                  95

CGG ATC CTG GAC TAT AGT GTT CAC GCT GAG CGC AAG GGC TCA CTG AGA        457
Arg Ile Leu Asp Tyr Ser Val His Ala Glu Arg Lys Gly Ser Leu Arg
                100                 105                 110

TAT GCC AAG GGT CAG AGT CAG ACC ATG GCA ACA CTG AAA GGC CTA GTG        505
Tyr Ala Lys Gly Gln Ser Gln Thr Met Ala Thr Leu Lys Gly Leu Val
            115                 120                 125

CAG AAG GGG GTG AAG GTG GAT CTG GGG ATC CCT CTG GAG CTT TGG GAT        553
Gln Lys Gly Val Lys Val Asp Leu Gly Ile Pro Leu Glu Leu Trp Asp
        130                 135                 140

GAG CCC AGC GTG GAG GTC ACA TAC CTC AAG AAG CAG TGT GAG ACC ATG        601
Glu Pro Ser Val Glu Val Thr Tyr Leu Lys Lys Gln Cys Glu Thr Met
```

-continued

```
           145                 150                 155
TTG GAG GAG TTT GAA GAC ATT GTG GGA GAC TGG TAC TTC CAC CAT CAG    649
Leu Glu Glu Phe Glu Asp Ile Val Gly Asp Trp Tyr Phe His His Gln
160                 165                 170                 175

GAG CAG CCC CTA CAA AAT TTT CTC TGT GAA GGT CAT GTG CTC CCA GCT    697
Glu Gln Pro Leu Gln Asn Phe Leu Cys Glu Gly His Val Leu Pro Ala
                180                 185                 190

GCT GAA ACT GCA TGT CTA CAG GAA ACT TGG ACT GGA AAG GAG ATC ACA    745
Ala Glu Thr Ala Cys Leu Gln Glu Thr Trp Thr Gly Lys Glu Ile Thr
            195                 200                 205

GAT GGG GAA GAG AAA ACA GAA GGG GAG GAA GAG CAG GAG GAG GAG GAG    793
Asp Gly Glu Glu Lys Thr Glu Gly Glu Glu Glu Gln Glu Glu Glu Glu
        210                 215                 220

GAA GAG GAG GAA GAG GAA GGG GGA GAC AAG ATG ACC AAG ACA GGA AGC    841
Glu Glu Glu Glu Glu Glu Gly Gly Asp Lys Met Thr Lys Thr Gly Ser
    225                 230                 235

CAC CCC AAA CTT GAC CGA GAA GAT CTT TGACCCTTGC CTTTGAGCCC          888
His Pro Lys Leu Asp Arg Glu Asp Leu
240                 245
```

CCAGGAGGGG AAGGGATCAT GGAGAGCCCT CTAAAGCCTG CACTCTCCCT GCTCCACAGC    948

TTTCAGGGTG TGTTTATGAG TGACTCCACC CAAGCTTGTA GCTGTTCTCT CCCATCTAAC   1008

CTCAGGCAAG ATCCTGGTGA ACAGCATGA CATGGCTTCT GGGGTGGAGG GTGGGGGTGG   1068

AGGTCCTGCT CCTAGAGATG AACTCTATCC AGCCCCTTAA TTGGCAGGTG TATGTGCTGA   1128

CAGTACTGAA AGCTTTCCTC TTTAACTGAT CCCACCCCCA CCCAAAAGTC AGCAGTGGCA   1188

CTGGAGCTGT GGGCTTTGGG GAAGTCACTT AGCTCCTTAA GGTCTGTTTT TAGACCCTTC   1248

CAAGGAAGAG GCCAGAACGG ACATTCTCTG CGATCTATAT ACATTGCCTG TATCCAGGAG   1308

GCTACACACC AGCAAACCGT GAAGGAGAAT GGGACACTGG GTCATGGCCT GGAGTTGCTG   1368

ATAATTTAGG TGGGATAGAT ACTTGGTCTA CTTAAGCTCA ATGTAACCCA GAGCCCACCA   1428

TATAGTTTTA TAGGTGCTCA ATTTTCTATA TCGCTATTAA ACTTTTTTCT TTTTTTCTAA   1488

AAAAAAAAAA AAAAGGGCGG CCGC                                          1512

(2) INFORMATION FOR SEQ ID NO:2:

(i) SEQUENCE CHARACTERISTICS:
        (A) LENGTH: 248 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Pro Val Arg Leu Gly Ile Leu Leu Phe Leu Phe Leu Ala Val
1               5                   10                  15

His Glu Ala Trp Ala Gly Met Leu Lys Glu Glu Asp Asp Thr Glu
            20                  25                  30

Arg Leu Pro Ser Lys Cys Glu Val Cys Lys Leu Leu Ser Thr Glu Leu
        35                  40                  45

Gln Ala Glu Leu Ser Arg Thr Gly Arg Ser Arg Glu Val Leu Glu Leu
    50                  55                  60

Gly Gln Val Leu Asp Thr Gly Lys Arg Lys Arg His Val Pro Tyr Ser
65                  70                  75                  80

Val Ser Glu Thr Arg Leu Glu Glu Ala Leu Glu Asn Leu Cys Glu Arg
                85                  90                  95

Ile Leu Asp Tyr Ser Val His Ala Glu Arg Lys Gly Ser Leu Arg Tyr
```

```
                      100                 105                 110
Ala Lys Gly Gln Ser Gln Thr Met Ala Thr Leu Lys Gly Leu Val Gln
            115                 120                 125

Lys Gly Val Lys Val Asp Leu Gly Ile Pro Leu Glu Leu Trp Asp Glu
    130                 135                 140

Pro Ser Val Glu Val Thr Tyr Leu Lys Lys Gln Cys Glu Thr Met Leu
145                 150                 155                 160

Glu Glu Phe Glu Asp Ile Val Gly Asp Trp Tyr Phe His His Gln Glu
                165                 170                 175

Gln Pro Leu Gln Asn Phe Leu Cys Glu Gly His Val Leu Pro Ala Ala
                180                 185                 190

Glu Thr Ala Cys Leu Gln Glu Thr Trp Thr Gly Lys Glu Ile Thr Asp
            195                 200                 205

Gly Glu Glu Lys Thr Glu Gly Glu Glu Gln Glu Glu Glu Glu
    210                 215                 220

Glu Glu Glu Glu Glu Gly Gly Asp Lys Met Thr Lys Thr Gly Ser His
225                 230                 235                 240

Pro Lys Leu Asp Arg Glu Asp Leu
                245
```

(2) INFORMATION FOR SEQ ID NO:3:

(i) SEQUENCE CHARACTERISTICS:
        (A) LENGTH: 744 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..744

(xi) SEQUENCE DESCRIPTION: SEQ ID NO:3:

```
ATG GGA CCT GTG CGG TTG GGA ATA TTG CTT TTC CTT TTT TTG GCC GTG      48
Met Gly Pro Val Arg Leu Gly Ile Leu Leu Phe Leu Phe Leu Ala Val
 1               5                  10                  15

CAC GAG GCT TGG GCT GGG ATG TTG AAG GAG GAG GAC GAT GAC ACA GAA      96
His Glu Ala Trp Ala Gly Met Leu Lys Glu Glu Asp Asp Asp Thr Glu
                20                  25                  30

CGC TTG CCC AGC AAA TGC GAA GTG TGT AAG CTG CTG AGC ACA GAG CTA     144
Arg Leu Pro Ser Lys Cys Glu Val Cys Lys Leu Leu Ser Thr Glu Leu
            35                  40                  45

CAG GCG GAA CTG AGT CGC ACC GGT CGA TCT CGA GAG GTG CTG GAG CTG     192
Gln Ala Glu Leu Ser Arg Thr Gly Arg Ser Arg Glu Val Leu Glu Leu
     50                  55                  60

GGG CAG GTG CTG GAT ACA GGC AAG AGG AAG AGA CAC GTG CCT TAC AGC     240
Gly Gln Val Leu Asp Thr Gly Lys Arg Lys Arg His Val Pro Tyr Ser
 65                  70                  75                  80

GTT TCA GAG ACA AGG CTG GAA GAG GCC TTA GAG AAT TTA TGT GAG CGG     288
Val Ser Glu Thr Arg Leu Glu Glu Ala Leu Glu Asn Leu Cys Glu Arg
                85                  90                  95

ATC CTG GAC TAT AGT GTT CAC GCT GAG CGC AAG GGC TCA CTG AGA TAT     336
Ile Leu Asp Tyr Ser Val His Ala Glu Arg Lys Gly Ser Leu Arg Tyr
                100                 105                 110

GCC AAG GGT CAG AGT CAG ACC ATG GCA ACA CTG AAA GGC CTA GTG CAG     384
Ala Lys Gly Gln Ser Gln Thr Met Ala Thr Leu Lys Gly Leu Val Gln
            115                 120                 125

AAG GGG GTG AAG GTG GAT CTG GGG ATC CCT CTG GAG CTT TGG GAT GAG     432
```

```
Lys Gly Val Lys Val Asp Leu Gly Ile Pro Leu Glu Leu Trp Asp Glu
            130                 135                 140

CCC AGC GTG GAG GTC ACA TAC CTC AAG AAG CAG TGT GAG ACC ATG TTG        480
Pro Ser Val Glu Val Thr Tyr Leu Lys Lys Gln Cys Glu Thr Met Leu
145                 150                 155                 160

GAG GAG TTT GAA GAC ATT GTG GGA GAC TGG TAC TTC CAC CAT CAG GAG        528
Glu Glu Phe Glu Asp Ile Val Gly Asp Trp Tyr Phe His His Gln Glu
                165                 170                 175

CAG CCC CTA CAA AAT TTT CTC TGT GAA GGT CAT GTG CTC CCA GCT GCT        576
Gln Pro Leu Gln Asn Phe Leu Cys Glu Gly His Val Leu Pro Ala Ala
            180                 185                 190

GAA ACT GCA TGT CTA CAG GAA ACT TGG ACT GGA AAG GAG ATC ACA GAT        624
Glu Thr Ala Cys Leu Gln Glu Thr Trp Thr Gly Lys Glu Ile Thr Asp
        195                 200                 205

GGG GAA GAG AAA ACA GAA GGG GAG GAA GAG CAG GAG GAG GAG GAG GAA        672
Gly Glu Glu Lys Thr Glu Gly Glu Glu Glu Gln Glu Glu Glu Glu Glu
210                 215                 220

GAG GAG GAA GAG GAA GGG GGA GAC AAG ATG ACC AAG ACA GGA AGC CAC        720
Glu Glu Glu Glu Glu Gly Gly Asp Lys Met Thr Lys Thr Gly Ser His
225                 230                 235                 240

CCC AAA CTT GAC CGA GAA GAT CTT                                        744
Pro Lys Leu Asp Arg Glu Asp Leu
                245
```

(2) INFORMATION FOR SEQ ID NO:4:

(i) SEQUENCE CHARACTERISTICS:
        (A) LENGTH: 226 amino acids
        (B) TYPE: amino acid
        (D) TOPOLOGY: linear (ii) MOLECULE TYPE: protein (xi) SEQUENCE DESCRIPTION: SEQ ID NO:4:

```
Met Leu Lys Glu Glu Asp Asp Thr Glu
1               5                   10

Arg Leu Pro Ser Lys Cys Glu Val Cys Lys Leu Leu Ser Thr Glu Leu
                15                  20                  25

Gln Ala Glu Leu Ser Arg Thr Gly Arg Ser Arg Glu Val Leu Glu Leu
            30                  35                  40

Gly Gln Val Leu Asp Thr Gly Lys Arg Lys Arg His Val Pro Tyr Ser
        45                  50                  55

Val Ser Glu Thr Arg Leu Glu Glu Ala Leu Glu Asn Leu Cys Glu Arg
    60                  65                  70

Ile Leu Asp Tyr Ser Val His Ala Glu Arg Lys Gly Ser Leu Arg Tyr
75                  80                  85                  90

Ala Lys Gly Gln Ser Gln Thr Met Ala Thr Leu Lys Gly Leu Val Gln
                95                  100                 105

Lys Gly Val Lys Val Asp Leu Gly Ile Pro Leu Glu Leu Trp Asp Glu
            110                 115                 120

Pro Ser Val Glu Val Thr Tyr Leu Lys Lys Gln Cys Glu Thr Met Leu
        125                 130                 135

Glu Glu Phe Glu Asp Ile Val Gly Asp Trp Tyr Phe His His Gln Glu
    140                 145                 150

Gln Pro Leu Gln Asn Phe Leu Cys Glu Gly His Val Leu Pro Ala Ala
155                 160                 165                 170

Glu Thr Ala Cys Leu Gln Glu Thr Trp Thr Gly Lys Glu Ile Thr Asp
                175                 180                 185
```

-continued

```
Gly Glu Glu Lys Thr Glu Gly Glu Glu Gln Glu Glu Glu Glu Glu
            190                 195                 200

Glu Glu Glu Glu Glu Gly Gly Asp Lys Met Thr Lys Thr Gly Ser His
        205                 210                 215

Pro Lys Leu Asp Arg Glu Asp Leu
    220                 225
```